United States Patent
Webster

(10) Patent No.: US 10,413,995 B2
(45) Date of Patent: Sep. 17, 2019

(54) METHODS AND SYSTEMS FOR CHARACTERIZING LASER MACHINING PROPERTIES BY MEASURING KEYHOLE DYNAMICS USING INTERFEROMETRY

(71) Applicant: IPG Photonics Corporation, Oxford, MA (US)

(72) Inventor: Paul J. L. Webster, Kingston (CA)

(73) Assignee: IPG PHOTONICS CORPORATION, Oxford, MA (US)

( * ) Notice: Subject to any disclaimer, the term of this patent is extended or adjusted under 35 U.S.C. 154(b) by 0 days.

(21) Appl. No.: 15/684,145

(22) Filed: Aug. 23, 2017

(65) Prior Publication Data
US 2018/0178320 A1      Jun. 28, 2018

Related U.S. Application Data

(63) Continuation of application No. 14/775,136, filed as application No. PCT/CA2014/000273 on Mar. 13, 2014, now Pat. No. 9,757,817.
(Continued)

(51) Int. Cl.
*G01B 11/02*     (2006.01)
*B23K 26/03*     (2006.01)
(Continued)

(52) U.S. Cl.
CPC ............. *B23K 26/032* (2013.01); *B23K 9/00* (2013.01); *B23K 10/02* (2013.01);
(Continued)

(58) Field of Classification Search
CPC .. B23K 26/032; B23K 26/082; B23K 26/244; B23K 26/0643; B23K 26/0648;
(Continued)

(56) References Cited

U.S. PATENT DOCUMENTS

| 3,303,319 A | 2/1967 | Steigerwald |
| 3,622,743 A | 11/1971 | Muncheryan |

(Continued)

FOREIGN PATENT DOCUMENTS

| CA | 2728950 A1 | 3/2012 |
| DE | 10155203 A1 | 6/2003 |

(Continued)

OTHER PUBLICATIONS

International Search Report and Written Opinion for International Application No. PCT/CA2011/050599 dated Dec. 8, 2011.
(Continued)

*Primary Examiner* — Kara E. Geisel
*Assistant Examiner* — Jonathon Cook
(74) *Attorney, Agent, or Firm* — Grossman, Tucker, Perreault & Pfleger, PLLC

(57) ABSTRACT

A method, apparatus, and system are provided to monitor and characterize the dynamics of a phase change region (PCR) created during laser welding, specifically keyhole welding, and other material modification processes, using low-coherence interferometry. By directing a measurement beam to multiple locations within and overlapping with the PCR, the system, apparatus, and method are used to determine, in real time, spatial and temporal characteristics of the weld such as keyhole depth, length, width, shape and whether the keyhole is unstable, closes or collapses. This information is important in determining the quality and material properties of a completed finished weld. It can also be used with feedback to modify the material modification process in real time.

23 Claims, 16 Drawing Sheets

Related U.S. Application Data

(60) Provisional application No. 61/778,592, filed on Mar. 13, 2013.

(51) Int. Cl.

| | | |
|---|---|---|
| G01B 5/00 | (2006.01) | |
| G01S 17/89 | (2006.01) | |
| G01B 11/24 | (2006.01) | |
| G01S 7/481 | (2006.01) | |
| B23K 26/082 | (2014.01) | |
| B23K 26/244 | (2014.01) | |
| G01N 21/954 | (2006.01) | |
| B23K 26/06 | (2014.01) | |
| B23K 26/14 | (2014.01) | |
| B23K 31/12 | (2006.01) | |
| G01B 11/22 | (2006.01) | |
| B23K 9/00 | (2006.01) | |
| B23K 10/02 | (2006.01) | |
| B23K 15/00 | (2006.01) | |
| B26F 1/26 | (2006.01) | |
| B26F 3/00 | (2006.01) | |

(52) U.S. Cl.
CPC ...... *B23K 15/0046* (2013.01); *B23K 26/0643* (2013.01); *B23K 26/0648* (2013.01); *B23K 26/082* (2015.10); *B23K 26/14* (2013.01); *B23K 26/244* (2015.10); *B23K 31/125* (2013.01); *G01B 5/0037* (2013.01); *G01B 11/22* (2013.01); *G01B 11/2441* (2013.01); *G01N 21/954* (2013.01); *G01S 7/4817* (2013.01); *G01S 17/89* (2013.01); *B26F 1/26* (2013.01); *B26F 3/004* (2013.01)

(58) Field of Classification Search
CPC .......... B23K 26/14; B23K 9/00; B23K 10/02; B23K 15/0046; B23K 31/125; G01B 5/0037; G01B 11/22; G01B 11/2441; G01B 9/02029; G01B 9/0209; G01B 9/02091; G01N 21/954; G01S 7/4817; G01S 17/89; B26F 1/26; B26F 3/004
USPC ....................................................... 356/496
See application file for complete search history.

(56) References Cited

U.S. PATENT DOCUMENTS

| | | | |
|---|---|---|---|
| 3,699,334 | A | 10/1972 | Cohen et al. |
| 4,618,262 | A | 10/1986 | Maydan et al. |
| 4,733,397 | A | 3/1988 | Gallagher et al. |
| 4,859,826 | A | 8/1989 | Hess, III |
| 4,892,098 | A | 1/1990 | Sauer |
| 5,339,323 | A | 8/1994 | Hunter et al. |
| 5,387,969 | A | 2/1995 | Marantette |
| 5,446,547 | A | 8/1995 | Guenther et al. |
| 5,631,171 | A | 5/1997 | Sandstrom et al. |
| 5,961,861 | A | 10/1999 | McCay et al. |
| 6,004,314 | A | 12/1999 | Wei et al. |
| 6,043,870 | A | 3/2000 | Chen |
| 6,454,761 | B1 | 9/2002 | Freedman |
| 6,485,413 | B1 | 11/2002 | Boppart et al. |
| 6,669,686 | B1 | 12/2003 | Singh |
| 6,755,819 | B1 | 6/2004 | Waelti |
| 6,763,259 | B1 | 7/2004 | Hauger et al. |
| 6,787,733 | B2 | 9/2004 | Lubatschowski et al. |
| 6,869,429 | B2 | 3/2005 | Singh |
| 7,411,682 | B2 | 8/2008 | Moshe |
| 7,436,520 | B1 | 10/2008 | Doerband |
| 7,619,746 | B2 | 11/2009 | DeLega |
| 7,688,453 | B2 | 3/2010 | Willby et al. |
| 7,884,924 | B2 | 2/2011 | Numata et al. |
| 7,924,435 | B2 | 4/2011 | Colonna De Lega et al. |
| 8,264,694 | B2 | 9/2012 | Mann et al. |
| 8,410,392 | B2 | 4/2013 | Kogel-Hollacher |
| 8,604,382 | B2 | 12/2013 | Yano et al. |
| 8,653,406 | B2 | 2/2014 | Gubler et al. |
| 8,735,768 | B2 * | 5/2014 | Urashima ............ B23K 26/032 219/121.63 |
| 8,822,875 | B2 | 9/2014 | Webster et al. |
| 8,982,339 | B2 | 3/2015 | Schonleber et al. |
| 9,457,428 | B2 | 10/2016 | Webster et al. |
| 2001/0008230 | A1 | 7/2001 | Keicher et al. |
| 2002/0153500 | A1 | 10/2002 | Fordahl et al. |
| 2003/0196994 | A1 | 10/2003 | Nikitin et al. |
| 2003/0227514 | A1 | 12/2003 | Nakashima |
| 2005/0027199 | A1 | 2/2005 | Clarke |
| 2006/0179992 | A1 | 8/2006 | Kermani |
| 2008/0017619 | A1 | 1/2008 | Yamakawa et al. |
| 2008/0281413 | A1 | 11/2008 | Culbertson et al. |
| 2010/0133247 | A1 | 6/2010 | Mazumder et al. |
| 2010/0142780 | A1 | 6/2010 | Yasuno et al. |
| 2010/0155375 | A1 | 6/2010 | Dietz et al. |
| 2010/0324542 | A1 | 12/2010 | Kurtz |
| 2011/0222024 | A1 | 9/2011 | Lu |
| 2011/0284508 | A1 | 11/2011 | Miura et al. |
| 2012/0138586 | A1 | 6/2012 | Webster et al. |
| 2012/0285936 | A1 | 11/2012 | Urashima et al. |
| 2012/0318775 | A1 | 12/2012 | Schwarz |
| 2013/0120740 | A1 | 5/2013 | Schonleber |
| 2014/0275986 | A1 | 9/2014 | Vertikov |
| 2015/0338210 | A1 | 11/2015 | Lessmuller et al. |
| 2016/0039045 | A1 | 2/2016 | Webster |
| 2016/0059347 | A1 | 3/2016 | Kogel-Hollacher et al. |
| 2016/0161752 | A1 | 6/2016 | Negoita et al. |
| 2016/0202045 | A1 | 7/2016 | Schonleber et al. |
| 2017/0120337 | A1 | 5/2017 | Kanko et al. |
| 2017/0120377 | A1 | 5/2017 | Webster et al. |

FOREIGN PATENT DOCUMENTS

| | | |
|---|---|---|
| DE | 102007032743 A1 | 1/2009 |
| DE | 102010016862 | 9/2011 |
| DE | 102013008269 | 11/2014 |
| EP | 1238744 A1 | 9/2002 |
| EP | 1977850 A1 | 10/2008 |
| WO | 2007038975 A1 | 12/2007 |
| WO | 2012-037694 | 3/2012 |
| WO | 2012152881 | 11/2012 |
| WO | 2013102912 A2 | 7/2013 |

OTHER PUBLICATIONS

Kanko, Jordan A., et al., "In situ morphology-based defect detection of selective laser melting through inline coherent imaging", Journal of Materials Processing Technology 231, 488-500. Dec. 29, 2015.
Leung, B.Y.C., et al., "Real-time coherent imaging of ultrafast ablation", Optical Society of America, CthG4 (2009).
Ohmi, M., et al., "In-situ observation of tissue laser ablation using optical coherence tomography", Optical and Quantum Electronics, vol. 37, 1175-1183 (2005).
Vakoc, B.J., et al., "Real-time microscopic visualization of tissue response to laser thermal therapy", Journal of Biomedical Optics, vol. 12 (2), 020501-1-020501-3 (Mar./Apr. 2007).
Weisner, M., et al., "Optical coherence tomography for process control of laser micromachining", Review of Scientific Instruments, vol. 81, 033705-1-033705-7 (2010).
Webster, P.J.L., et al., "Inter- and intrapulse dynamics and feedback control for laser machining", Optical Society of America, CF16 (2009).
Webster, P.J.L., et al., "In situ 24 kHz coherent imaging of morphology change in laser percussion drilling", Optics Letters, vol. 35, No. 5, 646-648 (2010).
Webster, P.J.L., et al., "High speed in situ depth profiling of ultrafast micromachining", Optics Express, vol. 15, No. 23, 14967-14972 (2007).
Yu, J.X.Z., et al., "High quality percussion drilling of silicon with a CW fiber laser", Proceedings of SPIE Photonics West: LASE, San Francisco, CA, (2010).

(56) References Cited

OTHER PUBLICATIONS

Muller, M.S., et al., "Ultrafast technology applied to optical coherence tomography" La Physique Au Canada, vol. 65, No. 2, 93-86 (2009).

Leung, B.Y.C., et al., "Real-time guidance of thermal and ultrashort pulsed laser ablation in hard tissue using inline coherent imaging", Lasers in Surgery and Medicine, vol. 44, No. 3, 249-256 (2012).

Webster, P.J.L., et al., "Automatic real-time guidance of laser machining with inline coherent imaging", J. Laser Appl., vol. 23, No. 2, 022001 (2011).

Buzug, T.M., et al., "Navigation concept for image-guided laser surgery", Proc Int. IEEE Conf. Mechatronics Robotics 1403-1408 (2004).

Hohlweg-Majert, B., et al., "Bone treatment laser-navigated surgery", Lasers Med. Sci., vol. 25(1), 67-71 (2010).

Stopp, S., et al., "A new concept for navigated laser surgery", Lasers Med. Sci., vol. 23(3), 261-266 (2008).

Stopp, S., et al., "A new approach for creating defined geometries by navigated laser ablation based on volumetric 3-D data", IEEE Trans. Biomed Eng., vol. 55(7), 1872-1880 (2008).

Rupprecht, S., et al., "Sensor-based laser ablation for tissue specific cutting: an experimental study", Lasers Med. Sci., vol. 19(2), 81-88 (2004).

Fercher, A.F., et al., "Optical coherence tomography—principles and applications", Rep. Prog. Phys., vol. 66(2), 239-303 (2003).

Boppart, S.A., et al., "High-resolution optical coherence tomography-guided laser ablation of surgical tissue", J. Surg. Res., vol. 82, 275-284 (1999).

Oh, W.Y., et al., "Ultrahigh-speed optical frequency domain imaging and application to laser ablation monitoring", Appl. Phys. Lett., vol. 88(10) 103902 (2006).

Wang, Y., et al., "Low-noise broadband light generation from optical fibers for use in high-resolution optical coherence tomography", J. Opt. Soc. Am. A., vol. 22(8), 1492-1499 (2005).

Bonora, S. et al., "Low-threshold ablation of enamel and dentin using ND:YAG laser assisted with chromophone with different pulse shapes", Proc. SPIE, vol. 4313, 23-30 (2004).

Li, Z.Z., et al., "Bone ablation with Er:YAG and CO2 laser: study of thermal and acoustic effects", Las. Surg. Med., vol. 12(1), 79-85 (1992).

Leech, P.W., "Laser ablation of multilayered hot stamping foil", J. Mater. Process. Technol. 209, 4281-4285 (2009).

Lausten, R., et al., "On-the-fly depth profiling during ablation with ultrashort laser pulses: a tool for accurate micromachining and laser surgery", Appl. Phys. Lett. 79(6), 884-886 (2001).

Webster, P.J.L., et al., "In-situ localization of machining dynamics with coherent microscopy", Canadian Laser Application Network (CLAN) Workshop, Mar. 12, 2009.

Webster, P.J.L., et al., "Coaxial real-time metrology and gas assisted laser micromachining: process development, stochastic behavior and feedback control", Proceedings of SPIE Photonics West MOEMS 759003-758003-10, San Francisco, CA (2010).

Webster, P.J.L., et al., "Guidance of hard tissue ablation by forward-viewing optical coherence tomography", Proceedings of SPIE, vol. 7554, 75540Z-75540Z-6 (2010).

Lindner, M.W., et al., "Spectral Radar: Optical Coherence Tomography in the Fourier Domain", in: Handbook of Optical Coherence Tomography, edited by E. Bourna and G.J. Teamey, Marcel Dekker, New York, pp. 335-357 (2002).

Webster, P.J.L., et al., "High speed observation of ultrafast machining dynamics", in Conference on Lasers and Electro-Optics p. CMF6 Optical Society of America, San Jose, CA (2008).

Webster, P.J.L., et al., "Inline coherent imaging of laser micromachining", International Symposium on Optomechatronic Technologies, Toronto, ON (2010).

Fraser, J.M., "In-situ coherent imaging to monitor and control laser processing", Harvard University Colloquium (2011).

Hofer, B., et al., "Signal post processing in frequency domain OCT and OCM using a filter bank approach", Proc. SPIE 6443, 644300 (2007).

Hofer, B., et al., "Dispersion encoded full range frequency domain optical coherence tomography", Optics Express, vol. 17 (1), 7-24 (2009).

Leung, B.Y.C., et al., "Real time Coherent Imaging of Ultrafast Ablation", Department of Physics, Engineering Physics and Astronomy, Queen's University, Kingston, Ontario, Canada, Jun. 4, 2009.

Webster, P.J.L., et al., "Inter- and Intra-pulse Dynamics & Feedback Control for Laser Machining", Queen's University, Kingston, Ontario, Canada.

Yu, J.X.Z., et al., "High-quality percussion drilling of silicon with a CW fiber laser", Department of Physics, Engineering Physics and Astronomy, Queen's University, Kingston, Ontario, Canada, Jan. 27, 2010.

Patel, N.A., et al., "Guidance of aortic ablation using optical coherence tomography", The International Journal of Cardiovascular Imagining 19, 171-178 (2003).

Wiesemann, W., "Process monitoring and closed-loop control", In: Landolt-Bornstein: Numerical Data and Functional Relationships in Science and Technology, Group VIII: Advanced Materials and Technologies, vol. 1: Laser Physics and Application, subvolume 1C: Laser Applications, Springer, pp. 243-275 (2004).

International Search Report and Written Opinion for PCT/CA2014/000273, dated Jun. 26, 2014.

Extended European Search Report for European Patent Application No. 147644437.1, dated Dec. 5, 2016.

Ngo, A., et al., "Laser Welding of Urinary Tissues, Ex Vivo, Using a Tunable Thulium Fiber Laser", SPIE 6078, Photonic Therapeutics and Diagnostics II, vol. 6078, 60781B-1-60781B-8 (2006).

Choi, E.S., et al., "Optical Coherence Tomography in Material Deformation by Using Short Pulse Laser Irradiation", SPIE, 6847, Coherence Domain Optical Methods and Optical Coherence Tomography in Biomedicine XII, 68470W-1-68470W-8 (2008).

Third Party Submission filed on Jun. 3, 2013 for U.S. Appl. No. 13/245,334.

Third Party Observation filed on Dec. 18, 2014 for EP Patent Application No. 11826290.6.

Schmitt, R., et al., "Inline process metrology system for the control of laser surface structuring processes", Physics Procedia 39, 814-822 (2012).

Schmitt, R., "Process monitoring in laser micro machining", Photonik International, 57-59 (2013).

Canadian Examiner's Requisition dated Dec. 15, 2016 for Canadian Patent Application No. 2, 728, 950.

Supplementary European Search Report for European Application No. EP11826290.6, dated Jun. 2, 2017.

International Search Report and Written Opinion, dated May 17, 2018, in related International Application No. PCT/US18/14218.

Matsunawa et al.; "Dynamics of Keyhole and Molten Pool in Laser Welding"; Journal of Laser Applications 10, 247 (1998); https://doi.org/10.2351/1.521858.

Gu, Hongping; "Real-Time Monitoring and Adaptive Control of CO2 Laser Beam Welding"; A thesis presented to the University of Waterloo; Waterloo, Ontario, Canada, 1998.

Postma, S., Postma, S., Aarts, R. G. K M., Meijer, J., & Jonker, J. B. (2002). "Penetration control in laser welding of sheet metal." Journal of Laser Applications, 14(4), 210-214. DOI: 10.2351/1.1493764.

Fabbro et al; "Keyhole Modeling During Laser Welding"; Journal of Applied Physics; vol. 87; No. 9; May 1, 2000; pp. 4075-4083.

Bardin et al; "Process Control of Laser Keyhole Welding"; International Congress of Applications of Lasers and Electro Optics 2004; 1008 (2004); doi: 10.2351/1.5060185; Published by Laser Institute of America; 11 pages.

Young, Thomas (1807). A Course of Lectures on Natural Philosophy and the Mechanical Arts.

Born, Max; Wolf, Emil (1999). Principles of Optics (7th expanded ed.).

Dilthey, U.; Handbuch zum BMBF-Projektverband "Qualifizierung von Laserverfahren" im Rahmen des Forderkonzeptes Laser 2000; DVS-Vert., 2000, ISBN 3-87155-906-7 along with English translation; pp. 117-120.

Annex from Communication dated Nov. 30, 2018 in corresponding European Patent Application No. 11826290.6.

(56) References Cited

OTHER PUBLICATIONS

Observations by third party mailed Jan. 31, 2019 in connection with corresponding European Patent Application No. 11826290.6.
Bautze et al; "Keyhole Depth is just a Distance"; Laser Technik Journal dated Apr. 2014, pp. 39-43.

* cited by examiner

METHODS AND SYSTEMS FOR CHARACTERIZING LASER MACHINING PROPERTIES BY MEASURING KEYHOLE DYNAMICS USING INTERFEROMETRY

FIELD

This invention relates to imaging using interferometry, including low-coherence interferometry, and to optical modification or measurement of materials, such as through the use of lasers in processes such as machining and welding.

BACKGROUND

Lasers are known to be important tools for processing a wide range of materials. In particular, lasers are very well suited to and see wide application for processing of metals, polymers, ceramics, semiconductors, composites and biological tissue. By focusing a laser beam, it can be possible to achieve improved precision of the laser's action in a direction transverse to the beam axis. However, localizing the laser's action in the axial direction of the beam can be difficult. During processes such as laser welding, a phase change region (PCR) is created where the material localized to the bonding region changes dynamically from solid to a liquid and/or a gas state and back to a solid again at the completion of the weld. In some cases the material may change multiple times between the various states and also interact with other substances present in the weld zone including other solids, liquids and gasses. Controlling this phase change region (PCR) is important to control the quality of the weld and the overall productivity of the welding system. The high spatial coherence of laser light allows good transverse control of the welding energy deposition, but thermal diffusion limits the achievable aspect ratio of welded features when the energy is transmitted through the material with conduction alone. For higher aspect ratio features, the more dynamic and unstable process of keyhole welding is used to allow the conversion of optical to thermal energy to occur deeper in the material. Here, axial control (depth of the PCR) is even more problematic. In keyhole welding, the depth of the PCR and the absorption of the laser may extend deep into the material (for example, depths from 10 micrometers to tens of millimeters). Here, the beam intensity is sufficient to melt the surface to open a vapor channel (also known as a capillary or "the keyhole") which allows the optical beam to penetrate deep into the material. Depending on the specific application, the keyhole may be narrow (e.g., less than 1 mm) but several millimeters deep and sustained with the application of optical power (for example in the range from 1-2 W to 20,000 W or more). As a result, the light-matter interaction region inside the PCR can be turbulent, unstable and highly stochastic. Unfortunately, instability of keyhole formation can lead to internal voids and high weld porosity resulting in weld failure, with potential catastrophic consequences. Similarly, keyhole instability can result in spatter that contaminates nearby system components, complicating the application of laser welding in systems such as vehicular transmissions. Weld quality verification is usually required, often using expensive ex-situ and destructive testing. Welding imaging solutions are offered but are limited in their capabilities and usually monitor regions either before or after the PCR, to track the weld joint, or record the top surface of the cooled weld joint.

SUMMARY

Some embodiments of the invention involve characterization of morphology, for example, including one or more of length, width, depth, size, shape, and aspect ratio of the keyhole and surrounding material over time by directing an interferometry measurement beam (including, for example, a low-coherence interferometry measurement beam) into the PCR and surrounding area. The beam may be moved along an x- or y-axis and/or O/p (i.e., theta/phi, angle may change from normal).

According to one aspect of the invention, there is provided an apparatus comprising: an imaging optical source that produces imaging light that is applied to a material processing system, wherein the material processing system implements a material modification process and creates a phase change region (PCR) in a material; at least one element that directs the imaging light at a plurality of imaging beam positions proximate the PCR; at least one input-output port that outputs a first component of the imaging light to an optical access port of the material processing system and that receives a reflection component of the imaging light; an optical combiner that combines the reflection component and at least another component of the imaging light to produce an interferometry output, the interferometry output based on a path length taken by the first component and the reflection component compared to a path length taken by the at least another component of the imaging light; and an interferometry output processor that processes the interferometry output to determine at least one characteristic of the PCR.

In some embodiments the apparatus may further comprise a material processing beam source that produces a material processing beam that is applied to the material in the material modification process, wherein the material processing beam creates the PCR in the material.

According to another aspect of the invention, there is provided an apparatus for modifying a sample, the apparatus comprising: a material processing beam source that produces a material processing beam that is applied to the sample at a sample location in a material modification process wherein the material processing beam creates a phase change region (PCR) in the sample; an imaging optical source that produces imaging light that is applied at a plurality of imaging beam positions proximate the PCR (i.e., in the vicinity of the PCR and/or within the PCR); an optical interferometer that produces an interferometry output for each imaging beam position using at least a component of the imaging light that is delivered to the sample, the interferometry output based on at least one optical path length to the sample compared to another optical path length; and an interferometry output processor that processes the interferometry outputs to determine at least one characteristic of the PCR.

According to another aspect of the invention, there is provided an apparatus for use with a material processing system that implements a material modification process and creates a phase change region (PCR) in a material, the material processing system having an optical access port, the apparatus comprising: an imaging optical source that produces imaging light that is applied at a plurality of imaging beam positions proximate the PCR; at least one input-output port that outputs a first component of the imaging light to the optical access port of the material processing system and that receives a reflection component of the imaging light; an optical combiner that combines the reflection component and at least another component of the imaging light to produce an interferometry output, the interferometry output based on a path length taken by the first component and the reflection component compared to a path length taken by the at least another component of the imaging light; and an interferometry output processor that processes the interferometry outputs to determine at least one characteristic of the PCR.

According to another aspect of the invention, there is provided a method comprising: applying an imaging light to a material processing system, wherein the material processing system implements a material modification process and creates a phase change region (PCR) in a material; using at least one element to direct the imaging light at a plurality of imaging beam positions proximate the PCR; outputting a first component of the imaging light to an optical access port of the material processing system and receiving a reflection component of the imaging light; combining the reflection component and at least another component of the imaging light to produce an interferometry output, the interferometry output based on a path length taken by the first component and the reflection component compared to a path length taken by the at least another component of the imaging light; and processing the interferometry output to determine at least one characteristic of the PCR.

In some embodiments, the method may further comprise applying a material processing beam to the material in the material modification process, wherein the material processing beam creates the PCR in the material.

According to another aspect of the invention, there is provided a method for modifying a sample, the apparatus comprising: producing a material processing beam that is applied to a sample at a sample location in a material modification process wherein the material processing beam creates a phase change region (PCR) in the sample; producing imaging light that is applied at a plurality of imaging beam positions proximate the PCR; producing an interferometry output for each imaging beam position using at least a component of the imaging light that is delivered to the sample, the interferometry output based on at least one optical path length to the sample compared to another optical path length; and processing the interferometry outputs to determine at least one characteristic of the PCR.

BRIEF DESCRIPTION OF THE DRAWINGS

Embodiments will be described below, by way of example, with reference to the accompanying drawings, wherein.

DETAILED DESCRIPTION

In all embodiments described herein, a material modification beam, also referred to as a material processing beam, is used. Examples of a material processing beam include a laser beam, an electron (or other particle) beam, plasma beam, electric arc, or water jet. Auxiliary laser beams and combinations of these (e.g., a laser beam guided by a water jet, hybrid laser arc welding) are also encompassed. Thus, whereas most embodiments are described as using a laser beam, it will be understood that the invention is not limited thereto.

As used herein, the terms "keyhole", "capillary", and "vapour channel" are considered to be equivalent and are intended to refer to the gaseous cavity that exists in a phase change region of a material during a material modification process using a material modification beam.

Figure 1:
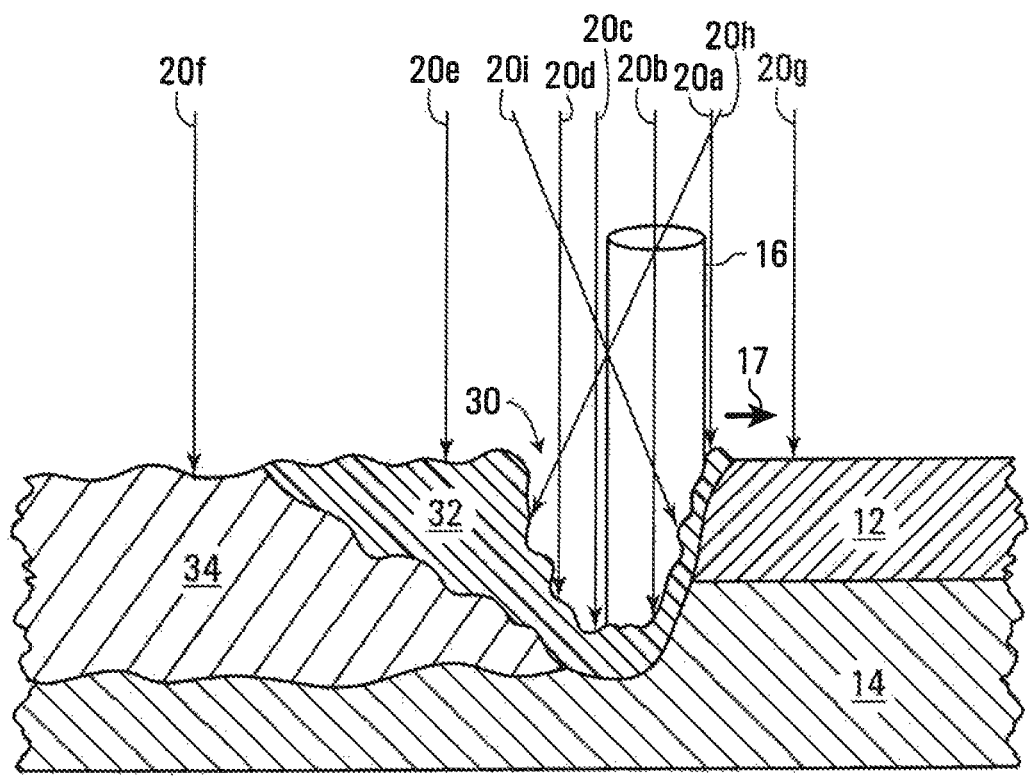
FIG. 1 is a cross section diagram of a material welding process featuring keyhole imaging in accordance with an embodiment of the invention.

FIG. 1 is a cross section diagram of a typical material welding process featuring coherent imaging in accordance with an embodiment of the invention. Two metal samples 12 and 14 are to be joined together in a continuous welding (CW), keyhole welding laser process. The laser beam 16 is moved across the surface in the direction indicated by arrow 17.

The PCR (phase change region) comprises a liquid region 32, a gas or keyhole region 30, and a bonded solid region 34, the solid having been reformed from the other two states. In general, if keyhole welding is occurring successfully, there will be three phases, as depicted in FIG. 1. However, in some embodiments, the apparatus and method are used to detect the lack of keyhole formation, in which case there may be only liquid and solid states, or only a solid state.

A plurality of imaging beams 20 (herein depicted as 20a through 20i) are introduced at multiple points and/or at multiple incident angles in, and optionally near, the PCR. In the specific example depicted, there are seven beams 20a, 20b, 20c, 20d, 20e, 20f, 20g that are substantially normal to samples, and two beams 20i, 20h that have incident angles that are not normal to the samples. The imaging beams 20 are used to generate measurements using low-coherence interferometry at each of the multiple points and/or multiple incident angles. While FIG. 1 shows a specific plurality of imaging beams 20 introduced at a specific set of points and incident angles, more generally, a plurality of measurements at some set of imaging beam positions are taken. The multiple imaging beam positions may involve one or a combination of:

one or more static beams;
one or more beams that are moved;
one or more beams normal to the sample location;
one or more beams whose angle is changed;
one or more beams that are moved and whose angles are changed; and
beams that originate from one or multiple light sources, including a light source that is multiplexed to produce multiple outputs.

In some embodiments, one of the plurality of imaging beam positions is created by the multiple internal reflection of an imaging beam inside of an optical element (which may also be referred to herein simply as an "optic") that the imaging light interacts with inside of the beam delivery system. This multiple reflection introduces additional optical path length (thus shifting the location of the reflection to a depth in the image and allowing it to be distinguished from the another beam measuring something else such as the keyhole depth) and a transverse shift of the focus of the beam. This allows for convenient simultaneous measurement of the top surface reference point(s) (TSRP) and weld depth. Top surface reference points are discussed in further detail below. An image showing such simultaneous measurement capability is shown in FIG. 4B. The reflection showing the TSRP is located at an indicated depth of approximately 650 μm.

Interferometry/Coherent Imaging Implementation

Each of a plurality of imaging beams (e.g., beams 20a-20i) originates from a semi-coherent light source, although as described above multiple beams may originate from a single light source. A very specific example of this type of light source is a superluminescent diode with a spectrum ranging from 820-860 nm and output power of 20 mW coupled into a single mode optical fiber such as Corning HI1780. Light sources meeting these criteria are commercially available and manufactured by Superlum Diodes Inc. (Ireland) and other manufacturers. The beam from the light source is carried, directed and manipulated through various media and components that might include fiber optic cables, air (or other gases), mirrors (or semi-reflective mirrors), lenses, or other optics. The fiber optic cables can be of the single-mode, multimode, and/or polarization maintaining types. The light source beam is split into two or more beams, for example using a semi-reflective mirror. One beam known as the imaging beam or sample beam is directed towards the sample; each of the beams depicted in the figure as 20a to 20i is such a sample beam. Another beam known as the reference beam is reflected off a reference surface (e.g., a mirror). The sample beam and the reference beam are then optically recombined, for example by the same semi-reflective mirror, so that they create and interference pattern. While a Michelson-style interferometer was just described, other interferometer configurations such as Mach-Zehnder (including the use of optical circulators), Sagnac, and common-path may also be applied in some embodiments. The interference pattern, I(k), will vary depending on the path length of the reflected imaging beam relative to the path length of the reference beam, $\Delta z$, according to the relationship $I(k)=A(k)[I(k)_{reference}+I(k)_{sample}+(\sqrt{I(k)_{sample} \cdot I(k)_{reference}})\cos(2k\Delta z)]$. These interferometry patterns are then captured and digitized using a commercially available spectrometer and camera such as the DeepView™ NIR spectrometer (BaySpec, Inc. San Jose, USA).

Additional established optical coherence tomography techniques and those from inline coherent imaging are then used to calculate depth relative to a known reference position. Specific examples of interferometry systems will be described below with reference to FIGS. 8 and 9.

Calculation of Keyhole/PCR Characteristics and/or Parameters

The following are examples of methods that may be used calculate keyhole PCR characteristics and/or parameters. A reference position(s) is established using points on the sample surface identified to be TSRPs. In the case where the sample is substantially flat, at least one TSRP can be used to define a top surface reference plane. Additional top surface reference points can be determined based on the top surface reference plane without taking corresponding additional measurements. Alternatively, multiple top surface reference points are used to calculate depth of the process.

The reference position, such as the TSRP, may be set, measured, or calibrated before, during, or after the welding process. This may be achieved by taking a baseline depth measurement or measurements at locations on the sample unaffected by the welding process, such as the location illuminated by beam 20g in FIG. 1. The TSRP can also be defined in real time by simultaneously imaging the top surface and keyhole bottom either through the use of multiple imaging channels or by enlarging the imaging spot to simultaneously or dynamically (i.e., sometimes the top, sometimes the bottom based on keyhole oscillations) cover both locations. In the simplest case, the TSRP can be determined by taking one or more measurements of the material immediately before the weld begins. If the material is sufficiently flat relative to the weld motion, then this initial measurement can define the TSRP for the rest of the weld. In other cases the TSRP is mechanically fixed at a specific distance or may be measured using other standard electrical, mechanical, or optical means. An example of this would be a beam delivery system that rolls across the workpiece(s). In this case, the virgin material surface would be a known distance away from the welding optics that is directly related to the distance between the unit's wheel(s) and the optics. Another example would be a welding system that utilizes a fixture or clamp to hold the workpiece(s). Again, since the distance between the optics and the fixture is known, the distance between the optics and the virgin surface of the material is known.

The imaging beams, such as beams 20 of FIG. 1, are used to measure, instantaneously and/or over a period of time, one or a combination of two or more of keyhole length, width, depth, surface shape, sub-surface profile, wall slope, collapse, instability, undercut, and other physical parameters of the PCR. Specific example methods of calculating each of these values will now be described. More generally, what constitutes length, width, depth, surface shape, sub-surface profile, wall slope, collapse, instability, undercut, or the other physical parameters of the PCR can be defined on an implementation-specific basis.

A single depth measurement is generally defined as the distance below the TSRP measured by the imaging beam. Note that depth can be a negative value if the measurement is above the TSRP.

For the following examples, the imaging beams are normal or close to normal to the sample surface.

Keyhole Depth—Keyhole depth for any instant in time is generally defined as the deepest point of the keyhole. This may be, for example, by taking multiple depth measurements within the keyhole and taking the maximum of these readings. Because the keyhole changes over time, in some embodiments, readings are taken in succession to determine how maximum depth changes over time. In practice, due to material properties and depth accuracy required, only a limited number of measurements in both position and time may be necessary. In other cases, a large number of measurements locations and/or measurement at high speed may be performed.

Location of Maximum Keyhole Depth—The location of maximum keyhole depth is the location at any instance in time from which the keyhole depth value is determined (i.e., the deepest location).

Average Keyhole Depth—The average keyhole depth is determined by taking the average of the individual keyhole depth values over some period of time. Other statistical techniques (e.g., standard deviation, median, min/max thresholds, higher order moments) may also be applied. Such statistical techniques can be used as direct indicators of weld stability, the probability of defects and therefore quality. Statistical snapshots of weld regions produced by image processors may also be used by feedback/process controllers to trigger annunciations and effect changes to weld parameters.

Keyhole Location—the relative positions of the leading edge, trailing edge, left side and right side of the keyhole relative to the processing (e.g., laser) beam.

Keyhole Length—Keyhole length is determined, for example, by calculating the furthest distance between two measurement beam readings that are below the TSRP and aligned with the axis of laser motion. For example, in FIG. 1, the keyhole length might be defined by the distance between measurement beams 20a and 20d.

Keyhole Width—Keyhole width may be similarly defined but with readings aligned perpendicular to the axis of laser motion.

Keyhole Surface Shape—The left and right side widths of the keyhole as measured relative to the processing laser at various points along the length of the keyhole.

Subsurface Keyhole Length and Width—Subsurface keyhole length and/or width can also be determined by calculating the length and/or width values relative to a plane at a predetermined distance below the TSRP.

Keyhole Profile—The depth of the keyhole measured at various points along the length of the keyhole.

Keyhole Wall Slope—Wall slope may be determined by calculating the slope of a line that fits two or more points on the wall of the keyhole. For example a line joining depth points 20a and 20b will give the slope of the front wall of the key hole. Similarly back and side wall slopes can be calculated.

Keyhole Collapse—Keyhole collapse can be determined if successive readings of keyhole depth temporarily or intermittently fail to meet or exceed some specified value.

Keyhole Instability—Keyhole instability can be determined from the variability of successive keyhole depth readings. Other calculations using coherent imaging may also be performed.

All of the examples above rely on imaging beams that are normal or substantially normal to the plane of the sample surface. In some cases it may be advantageous to take coherent imaging readings at angles that are not normal to the plane of the sample surface. Readings from imaging beams 20h and 20i of FIG. 1 would be examples of this. For example, in some embodiments, these off-normal imaging beams are used to determine or contribute to the determination of one or more of wall instability, partial keyhole collapse or situations that could lead to voids or porosity in a welding process. Particularly at high welding speeds at deeper depths, the keyhole vapour channel may undercut some of the liquid (towards the trailing edge of the weld) such that there is not a direct optical path to the bottom of the keyhole that is also normal to the material surface. This situation is particularly vulnerable to unstable pathological behaviour and may be detected by comparing signals from imaging beams 20b and 20h (or one similarly angled to reach the bottom of a undercut keyhole).

The dynamics of the liquid region of the PCR are examined. This can be done, for example, by taking multiple imaging beam measurements in and around where the liquid phase region is expected to be located. For the example of FIG. 1, multiple imaging beam measurements near imaging beam 20e may be used to look at the slope, changes, waves, or other characteristics of the liquid.

In some embodiments, the interface between the liquid/solid region of the PCR is located using the measurements. In a specific example, multiple imaging beam measurements are taken in and around where the interface is expected to be located (for example in and around the location of beams 20e, 20f of FIG. 1). The liquid will oscillate and detectably change its position whereas the solid region will be static, thus producing measurable contrast between the two phases.

In some embodiments, waves are excited and generated in the liquid region of the PCR using acoustic and/or optical energy source techniques to assist with generating imaging contrast and understanding PCR geometry, dynamics, and characteristics such as viscosity. For example, an acoustic vibration may be excited in the liquid at a frequency that is smaller than the imaging sample rate. An imaging beam observing such a liquid region would be able to measure the phase and amplitude of the geometric distortion that follows the acoustic vibration, thereby confirming the liquid state of the point being imaged.

In some embodiments of the invention, at least one of the plurality of imaging beams positions is outside the PCR. Beams 20f and 20g are examples of this in FIG. 1.

In some embodiments of the invention, light is applied to at least two of the plurality of imaging beams positions simultaneously. The multiple imaging beams can be generated in this case using multiple beam sources, or by using a single beam source and one or more splitters.

In some embodiments of the invention, light is applied to at least two of the plurality of imaging beam positions sequentially. The sequentially applied imaging beams can be generated using multiple beam sources that are activated in sequence, or by using a single beam source that is reconfigured to produce each of the beams in sequence.

In some embodiments of the invention, the plurality of imaging beam positions are achieved by changing the position and/or angle of at least one imaging beam relative to the processing beam during the welding process.

In some embodiments of the invention, the number of positions where the plurality of imaging beams is applied to the sample is changed during the welding process.

In some embodiments of the invention, at least one of the plurality of imaging beam positions does not have an incident position that is on a line formed by the material processing beam. For example, in FIG. 1, laser beam 16 moves in direction 17 and traces out a path. One or more of the imaging beams can be applied off this path. This can be used, for example, to determine keyhole width.

In some embodiments of the invention, imaging light applied to at least one of the plurality of imaging beams positions is used to determine the width or diameter of the keyhole when viewed from the same direction as the material processing (e.g., laser) beam is applied.

In some embodiments of the invention, imaging light applied to at least one of the plurality of imaging beam positions is focused to a diameter that is smaller than the diameter of the laser beam.

In some embodiments of the invention, imaging light applied to at least one of the plurality of imaging beam positions is focused to a diameter that is similar to the diameter of the laser beam.

In some embodiments of the invention, imaging light applied to at least one of the plurality of imaging beam positions is focused to a diameter that is larger than the diameter of the laser beam.

In some embodiments of the invention, imaging light applied to at least one of the plurality of imaging beam positions is focused to a diameter that encompasses the PCR.

In some embodiments of the invention, imaging light applied to at least one of the plurality of imaging beam positions is focused to a diameter that is larger than the PCR.

In some embodiments of the invention, imaging light applied to at least one of the plurality of imaging beam positions is used to take successive readings at a frequency of approximately 10 Hz or more.

In some embodiments of the invention, imaging light applied to at least one of the plurality of imaging beam positions is used to take successive readings at a frequency of approximately 100 Hz or more.

In some embodiments of the invention, imaging light applied to at least one of the plurality of imaging beam positions is used to take successive readings at a frequency of approximately 1 kHz or more.

In some embodiments of the invention, imaging light applied to at least one of the plurality of imaging beam positions is used to take successive readings at a frequency of approximately 10 kHz or more.

In some embodiments of the invention, imaging light applied to at least one of the plurality of imaging beam positions is used to take successive readings at a frequency of approximately 100 kHz or more.

In some embodiments of the invention, imaging light applied to at least one of the plurality of imaging beam positions is used to take successive readings at a frequency of approximately 1 MHz or more.

In some embodiments of the invention, imaging light applied to at least one of the plurality of imaging beam positions is used to determine the maximum depth achieved by the keyhole over a period of time. In some embodiments, this determination is used to control at least one parameter of the welding process to reduce the number of instances where welding will penetrate beyond a specified depth and/or into a specified material, including reducing the number of instances to zero.

In some embodiments of the invention, imaging light applied to at least one of the plurality of imaging beam positions is used to determine the minimum depth achieved by the keyhole over a period of time. In some embodiments, this determination is used to control at least one parameter of the welding process to reduce the number of instances where welding fails to penetrate beyond a specified depth and/or into a specified material, including reducing the number of instances to zero.

In some embodiments of the invention, imaging light applied to at least one of the plurality of imaging beam positions is used to determine the shape and size of the keyhole over time.

In some embodiments of the invention, imaging light applied to at least one of the plurality of imaging beam positions is used to determine if the keyhole collapses or fails to maintain a specified depth.

In some embodiments of the invention, imaging light applied to at least one of the plurality of imaging beam positions is used to calculate an optimal speed for the welding process.

In some embodiments of the invention, imaging light applied to at least one of the plurality of imaging beam positions is used to calculate an output power level for the laser beam.

In some embodiments of the invention, measurements for at least one of the plurality of imaging beam positions are processed, output, and fed back to the laser process control system to provide closed loop operation.

Figure 2:
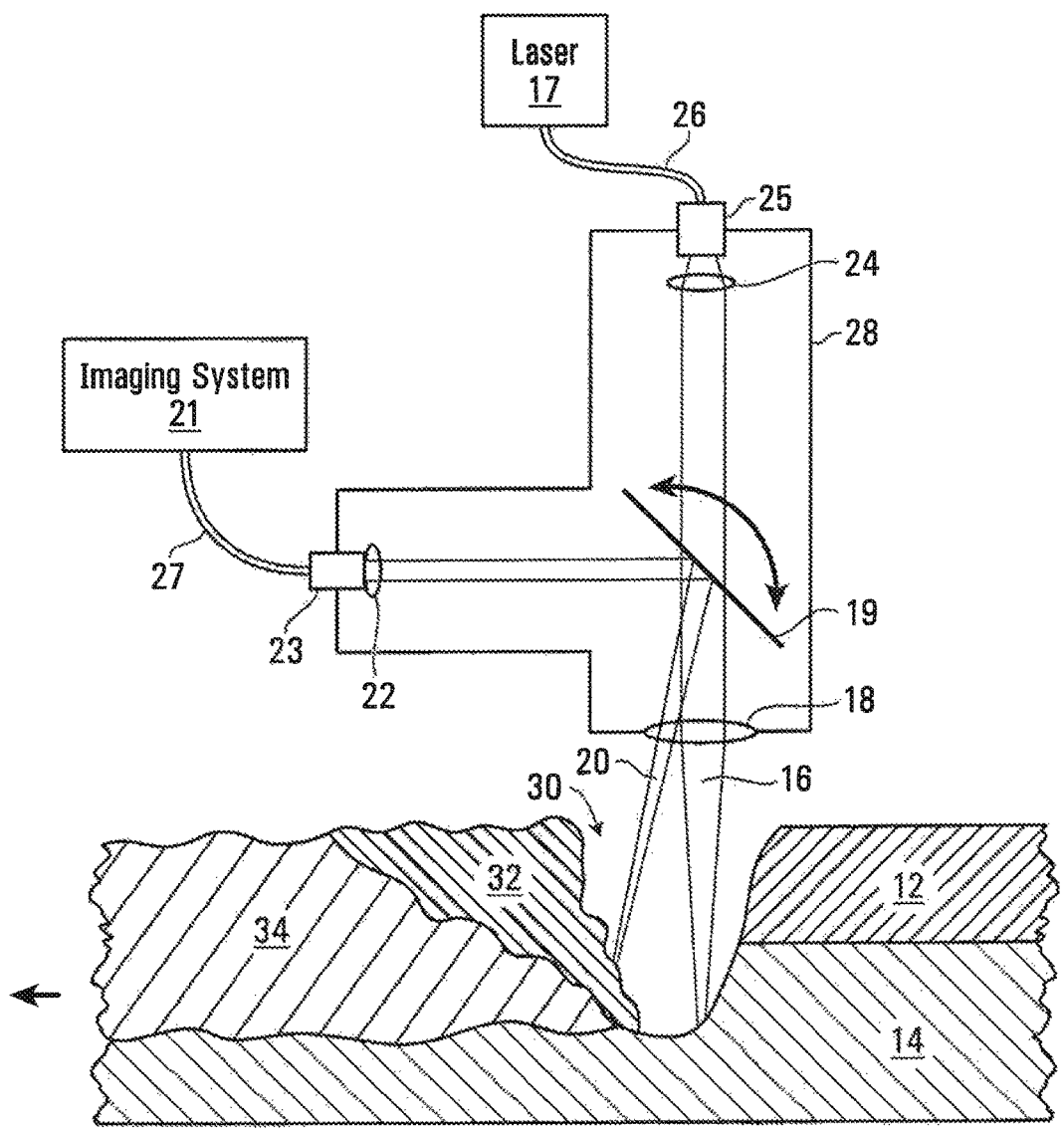
FIG. 2 is a schematic diagram of an apparatus that implements keyhole imaging in a material welding process, according to one embodiment.

FIG. 2 is a schematic diagram of an example of an apparatus that implements the coherent imaging in a material welding process. A material processing laser 17 produces a laser beam that is carried via a fiber optic cable 26 and connects through fiber attachment connector 25 to a laser head 28 which outputs laser beam 16. Embodiments described herein involve the use of a laser. The laser beam 16 is collimated by optic 24 and focused by optic 18 such that keyhole welding is achieved on the sample 12, 14. PCR 30, 32, 34 is depicted. A movable dichroic mirror 19 is shown.

A low-coherence interferometry imaging light source 21 produces imaging light that is carried via fiber optic cable 27 and connected through fiber attachment connector 23 to the laser head 28 where the imaging light is used to form an imaging beam 20. A collimating lens 22 directs the imaging beam 20 towards the mirror 19. The mirror 19 is actuated by a motorized system (not shown) such that the imaging beam 20 can be directed to multiple locations within the PCR 30 on the sample 12, 14.

In the illustrated example, the laser and the imaging beam (more generally light applied to at least one of the imaging beam positions) are focussed by a common focusing lens 18. In some embodiments of the invention the imaging beam 20 and laser beam 16 may each have their own separate focusing lenses which focus the beams before they are combined by mirror 19 and then delivered to the sample 12, 14. This may be particularly useful in some applications as it separates the optical requirements for imaging (e.g., multiple, possibly aspheric optical elements for field distortion reduction) and high power beam delivery optical requirements (minimal focal shift and power absorption). It also makes it easier to position a scanning device near the back focal position of a scanning lens, which is often desired for reducing optical path distortion when using telecentric scanning optics.

The scanning device is used to change the angle and/or position of the imaging beam and/or the processing beam. Examples of a scanning device are a galvanometer-mirror scanner (e.g., available from SCANLAB AG in Germany), a piezoelectrically actuated mirror, and a motor actuated mirror. A scanning lens is an optical device that is used in conjunction with or as a part of the scanning device to direct an optical beam. An example of a scanning lens is an LSM05 from Thorlabs Inc. (Newton, USA).

Embodiments described herein provide adjustment (automatic or otherwise) of the imaging beam's position relative to the processing beam, to compensate for motion/misalignment. For example, such adjustment may be carried out automatically, to adjust the imaging beam for changes in the velocity of the processing beam, and/or changes in the direction of the processing beam, and/or changes in the relative velocity between the beam delivery system and the workpiece, and/or changes in the process beam velocity and/or the velocity of the process beam's focus relative to the workpiece. In some embodiments the imaging beam may be adjusted to compensate for flexing and dynamic misalignment in the processing beam head and/or motion system. In some embodiments, the scanning device is used to adjust the imaging beam's position to compensate for flexing and dynamic misalignment of the head, the optics contained therein, and any motion system, such as, e.g., a robot or gantry motor that is utilized to effect the material modification process.

In some embodiments of the invention, an auxiliary measurement system that uses electronic, mechanical, optical, and/or capacitive techniques is provided. It is used, for example, to determine the distance from the laser head to the sample, and this information used as part of the interferometry and/or feedback processing.

For example, in some embodiments, at least one imaging beam is used to determine depth of the processing beam penetration in a material, i.e., depth of the keyhole. In such an embodiment the at least one imaging beam position is inside the keyhole. In various embodiments the at least one imaging beam position inside the keyhole is used together with at least one other measure to determine the depth of the keyhole. The at least one other measure may be obtained, for example, using a mechanical sensor in contact with a surface of the material being modified, an electronic sensor, a capacitive sensor, or optically. For example, in some embodiments, at least two imaging beam positions include a position outside the keyhole and a position inside the keyhole.

Determination of keyhole depth according to embodiments described herein may be carried out simultaneously during the material modification process. Such determination provides for dynamic control of the material modification process, thereby providing quality control, and improving quality.

The imaging beams are used to measure, either on a one time basis, once per workpiece basis, over a period of time, at regular or pre-set intervals, continuously, or substantially continuously, one or a combination of two or more keyhole features or parameters. The keyhole features, which are dynamic as they may change throughout the material modification process, include, but are not limited to, keyhole depth, location of maximum keyhole depth, average keyhole depth, keyhole location, keyhole width, keyhole length, surface shape, subsurface shape, subsurface keyhole length, subsurface keyhole width, wall slope, sidewall angle, keyhole collapse, keyhole stability, dynamics of liquid region of the PCR, location of interface between liquid and solid region, other physical parameters of the PCR.

Embodiments described herein allow dynamic and simultaneous, or substantially simultaneous, tracking of the material modification process, to achieve greater control of the process and higher quality results. In some embodiments, such tracking is carried out in respect of the processing beam, and accordingly at least one imaging beam is substantially aligned with the processing beam. In other embodiments, such tracking is carried out with respect to the PCR, and in particular, in respect of one or more dynamic keyhole features such as those described above. Accordingly, in such embodiments, the imaging beam is aligned so as to determine the one or more dynamic keyhole feature(s). Such alignment of the imaging beam may not be with processing beam; rather, in such embodiments the imaging beam may track the PCR (i.e., a PCR feature) optionally by a selected distance or with an offset determined so as to optimize the tracking.

The embodiments discussed in the description of FIG. 1 may be implemented using the arrangement of FIG. 2.

Figure 3:
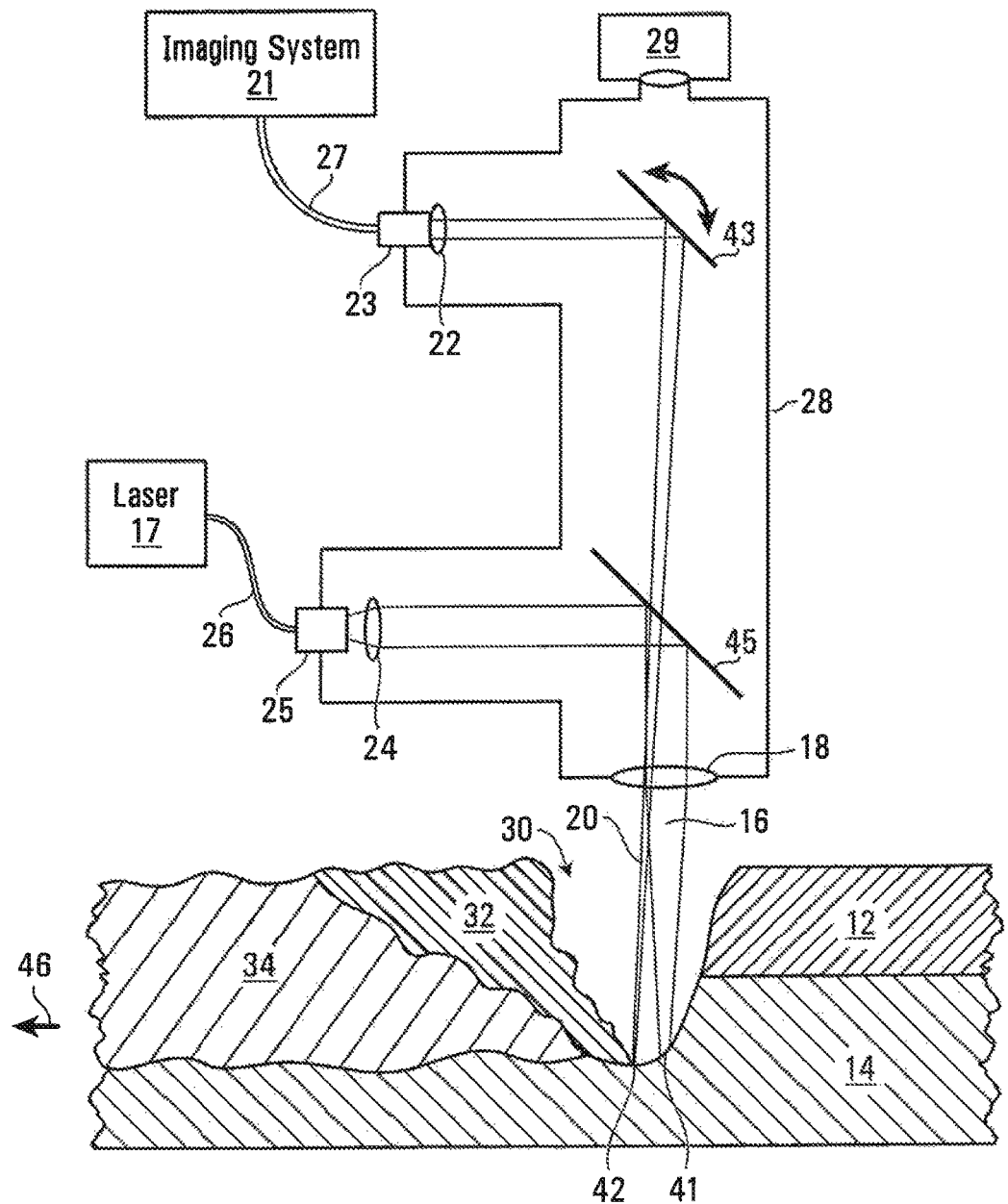
FIG. 3 is a schematic diagram of another apparatus that implements keyhole imaging in a material welding process, according to another embodiment, similar to the apparatus used to generate the images in FIGS. 4A-4E.

FIG. 3 is a schematic diagram of an example of another apparatus that implements the coherent imaging in a material welding process. A material processing laser 17 produces a laser output that is carried via a fiber optic cable 26 and connects at fiber optic connector 25 to a laser head 28 which outputs laser beam 16. A laser beam 16 is substantially collimated by optic 24, reflected by dichroic mirror 45 and then focused by optic 18 such that keyhole welding is achieved on the sample 12, 14. In some embodiments, mirror 45 is a movable mirror.

An imaging system 21 produces imaging light that is carried via fiber optic cable 27 and connected to fiber optic connector 23 to the laser head 28 where the imaging light is used to form an imaging beam 20. A collimating lens 22 substantially collimates the imaging beam and directs the imaging beam 20 towards the mirror 43. Adjustment of the relative positions and angles of 28, 27, 23, and 22 may be used to control the position and focal plane of the imaging beam. A movable mirror is shown at 43. The mirror 43 is actuated by a motorized system (not shown) such that the imaging beam 20 can be directed to multiple locations within the PCR 30, 32, 34 on the sample 12, 14. Instead of or in addition to a motorized mirror, an acousto-optic deflector, electro-optic deflector, or other device known to those of ordinary skill in the art to statically or dynamically change the angle of a beam could be used. In some cases, additional mirrors may be used to fold the beam path to allow it to fit into smaller linear spaces.

The movable mirror 43 and the dichroic mirror 45 are used to allow the laser beam and the imaging beam to be directed towards the sample and closely aligned. Depending on the angles of the mirrors 43, 45, at a given instant in time, the laser beam and imaging beam may be parallel, or at some angle relative to each other.

The imaging beam 20 is used to measure, over a period of time, one or a combination of two or more of the length, width, depth, surface shape, sub-surface shape, sidewall slope, collapse, instability, and/or other physical parameters of the PCR 30, 32, 34.

The embodiments discussed in the description of FIG. 1 may be implemented using the arrangement of FIG. 3.

Features denoted by reference characters 41, 42, 46 appearing in FIG. 3 will be detailed below in the discussion of working examples.

In some embodiments of the invention, a sacrificial covering glass is provided to protect the rest of the optics from emissions from the material modification process. The use of cover glass in laser materials processing is widely known and used by those of ordinary skill in the art.

In some embodiments of the invention, a cross jet of gas from one or a plurality of gas-fed pressurized orifices (known by some as an air knife) is employed to protect the optics from emissions from the material modification process by blowing them away. The use of a cross jet is widely known and used by those of ordinary skill in the art.

In some embodiments of the invention, a cover gas applied by one or more nozzles located above and/or below the workpiece and is employed to produce/prevent specific chemical effects (e.g., reduce oxidation) on the material being modified. The use of a cover gas is widely known and used by those of ordinary skill in the art.

The use of cover and cross jet gases may also provide the benefit of suppressing the amount of plasma and/or debris inside the beam path, which changes how the energy from the high power processing beam is absorbed in the sample.

Coherent imaging is particularly well suited to observing and controlling high energy material modification processes for several reasons. It is resistant to sensing process light, it is virtually immune to blackbody radiation, it has high sensitivity, high dynamic range, high speed, and is easy to integrate into existing optical systems.

Use of Auxiliary Measurement System to Influence the Feedback Output

In some embodiments, the beam delivery system may be modular to allow multiple configurations of optics, gas, material processing beams, and instrumentation to be used. Such instrumentation includes auxiliary measurement tools that can be used to influence the feedback and/or imaging output. Several examples follow:

1. The beam delivery system may use an auxiliary capacitive sensor to determine its separation from the sample.
2. The beam delivery system may include additional ports to add auxiliary instrumentation such as a co-axial camera and/or a laser triangulation system.
3. Structured light topology is an extension of laser triangulation and can also be used in conjunction with the beam delivery system for auxiliary measurements of the workpiece.
4. The feedback controller may also receive information from auxiliary equipment mentioned in the previous points and incorporate this information into the feedback output it gives to the process control system.
5. The image processor may also receive information from auxiliary equipment mentioned in the previous points and incorporate this information into the processing algorithms that it uses. For example, if the working separation distance between the delivery optics and the sample is detected to have increased by 1 mm, then the image processor can subtract 1 mm from the measurements of weld depth that it produces.

Compensation for Gas Pressure in the Coherent Imaging Beam Path

In some embodiments, optical path length compensation for gas pressure in the coherent imaging beam path is performed. The process controller and/or image processor may receive inputs from one or more pressure sensors that read the ambient pressure inside locations in the beam delivery system. Gas pressure changes the optical path length registered by the coherent imaging system. In some embodiments, these measurements are used to digitally (i.e., in processing the signal electrically or in software) or physically (e.g., by modifying the reference arm length) compensate for optical path length changes due to high pressure gas.

The amount of correction required is obtainable by fixing the location of the process head relative to a solid object and gradually pressurizing the head while tracking the apparent location of the surface. Thus a mapping of path length error as a function of head pressure can be obtained. Similarly, if the gas composition has a significant effect on the path length, this too can be simulated and measured in the same way. After programming this mapping into the process controller/image processor, it can then apply the necessary correction based on the measured pressure inputs.

Compensating for Optical Path Length Changes Resulting from Scanning the Imaging/Processing Beams In some embodiments, compensation for optical path length changes resulting from scanning the imaging/processing beams is performed. This can be done digitally and/or physically by adjusting an optical path length in the interferometer. This can be done, for example, by mirrors or by adding glass.

In some embodiments of the invention, the optical path length imaging beam on the sample is physically modified as a consequence of directing it to a different location on the sample, even if the sample height itself is not changing. This results in a distortion of the morphological data that the imaging system returns. While this can be corrected digitally in some cases, it may also be beneficial to correct for it physically, especially if the distortion is large. Alternatively, it may also be advantageous to intentionally distort the imaging field in order for it to conform to a material geometry that is not flat. The decision whether or not to take any of these approaches is application specific.

The first step to a correction is to measure the distortion. This is accomplished by moving the imaging beam to several locations on an object that is known to be flat, measuring the apparent height of the object in the coherent imaging system and subtracting the desired profile from these results. This data yields the error between the uncorrected and desired profiles.

The next step is to apply the correction. Digitally, this can be accomplished by addition of the known error at given positions to the future measurements at or around those positions. Error maps can be interpolated beforehand or in real time. Physically, distortion correction can be accomplished by manual or automated addition of optical materials to the reference path. This includes modifying the reference arm delay line length. In production, this can be co-ordinated with the scanning device. For example some scanning devices (such as a Cambridge Technology FlexScan-3D™, Cambridge Technology, Inc., Bedford, USA) utilize a Z-axis actuator to control the focal distance of the laser beam. The control signal for this actuator can be utilized as a command signal (e.g., via digital/analog scaling and subtraction) for the reference arm of the coherent imaging system.

Acoustic Excitation to Detect Liquid Vs. Solid Phases

In some embodiments, acoustic excitation is employed to detect liquid vs. solid phases. This might be used, for example, to provide an indication of the viscosity of the melt. Coherent imaging can sense the frequency and amplitude of a vibrating melt pool by monitoring its axial/transverse position and/or its reflectivity (which indicates, amongst other things, the radius of curvature of its surface). If vibration of a melt pool can be excited by optical (e.g., laser) or mechanical (e.g., an acoustic transducer) means, then coherent imaging is able to sense the presence of these vibrations, their frequency and/or their amplitude. This can be used to measure the viscosity of the melt pool in a certain region and to distinguish between liquid and solid metal.

For example, immediately after a spot weld occurs, a molten pool of metal is left oscillating. Coherent imaging data can determine the period and/or phase of the oscillation of the melt pool. This period is characteristic of and can therefore be used to determine at least one of the melt viscosity, material type, material state, and geometry. By sensing the period, (in this case) one can infer that the melt pool width is decreasing over time.

Figure 5:
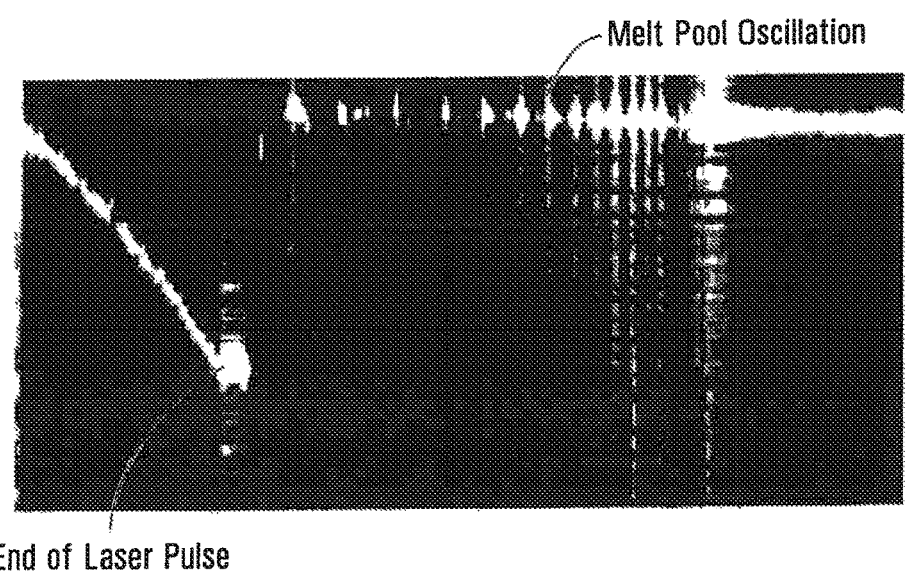
FIG. 5 shows an example of an image of a laser spot weld.

FIG. 5 shows an example of a coherent image of a laser spot weld. The keyhole is initially opened and increases in depth until the laser pulse (550 us duration, 1 kW intensity) is terminated at about a quarter of the way into the image. The keyhole remains open for a few tens of microseconds until it is filled in by liquid metal. The liquid metal oscillates which can be seen by the repetitive enhancement and reduction of the signal. Notably, the period of the oscillation is steadily reduced as the size of the oscillating weld pool shrinks due to the periphery fusing.

Detecting Spiking in Weld Depth

In some embodiments, spiking in weld depth is detected, and used as an indicator of the presence of porosity in the weld. Porosity indicates strength/longevity and sometimes even corrosion resistance of the weld. It is known to those of ordinary skill in the art that a welding phenomenon called "spiking" exists. Spiking is characterized by rapid, momentary enhancements in the weld penetration depth. In post-weld destructive testing, spiking appears as an inconsistent weld depth with one or many narrow depth enhancements. The underlying cause of spiking is dynamic instability and chaotic behaviour of the materials in and around the keyhole. Coherent imaging techniques are fast enough and have high enough spatial resolution to detect the rapid and momentary enhancements in depth that are the spiking phenomenon. Consequently, coherent imaging techniques can sense keyhole instability.

Also associated with keyhole instability are weld defects such as porosity and bad mixing of dissimilar materials. There is a correlation between the appearance of spiking dynamic behaviour as sensed by coherent imaging techniques and the presence of porosity in a weld. Therefore, by observing the keyhole dynamics of welding, coherent imaging can detect the presence of porosity in the weld.

Furthermore, by sensing the phase of keyhole oscillations with coherent imaging, the process controller can be made to synchronously or asynchronously drive the keyhole oscillations by modulating the power of the high power laser, or through the application of another energy source such as from an ultrasonic transducer.

Zinc is widely used to inhibit corrosion on a variety of metal products. The low vaporization temperature of zinc presents significant challenges to welding of materials that contain zinc (e.g., galvanized steel). The explosive vaporization of zinc can eject material from the phase change region and is difficult to predict. This can result in underfill and unwanted weld depth enhancements. Coherent imaging can sense the occurrence of a gas phase explosion or similar transient and generate an annunciation that can be used to warn the user or a process controller that a gas phase explosion or similar transient may have compromised the quality of a weld. In coherent imaging, this condition looks like a sudden enhancement of the weld depth over the course of a time period, for example ~5 ms. Coherent imaging can also sense keyhole instability from small transients before a large transient and generate a warning of risk of a future large transient or large gas phase explosion. This may be thought of in the way that small seismic events may herald the coming of a large one in the future. In this case, corrective action can be taken to prevent a large zinc explosion by, for example, reducing the power of the processing beam and/or increasing the gap between two parts to be welded by e.g., tens of micrometers. While zinc is referred to in this paragraph, other materials may have the same effect.

Figure 10:
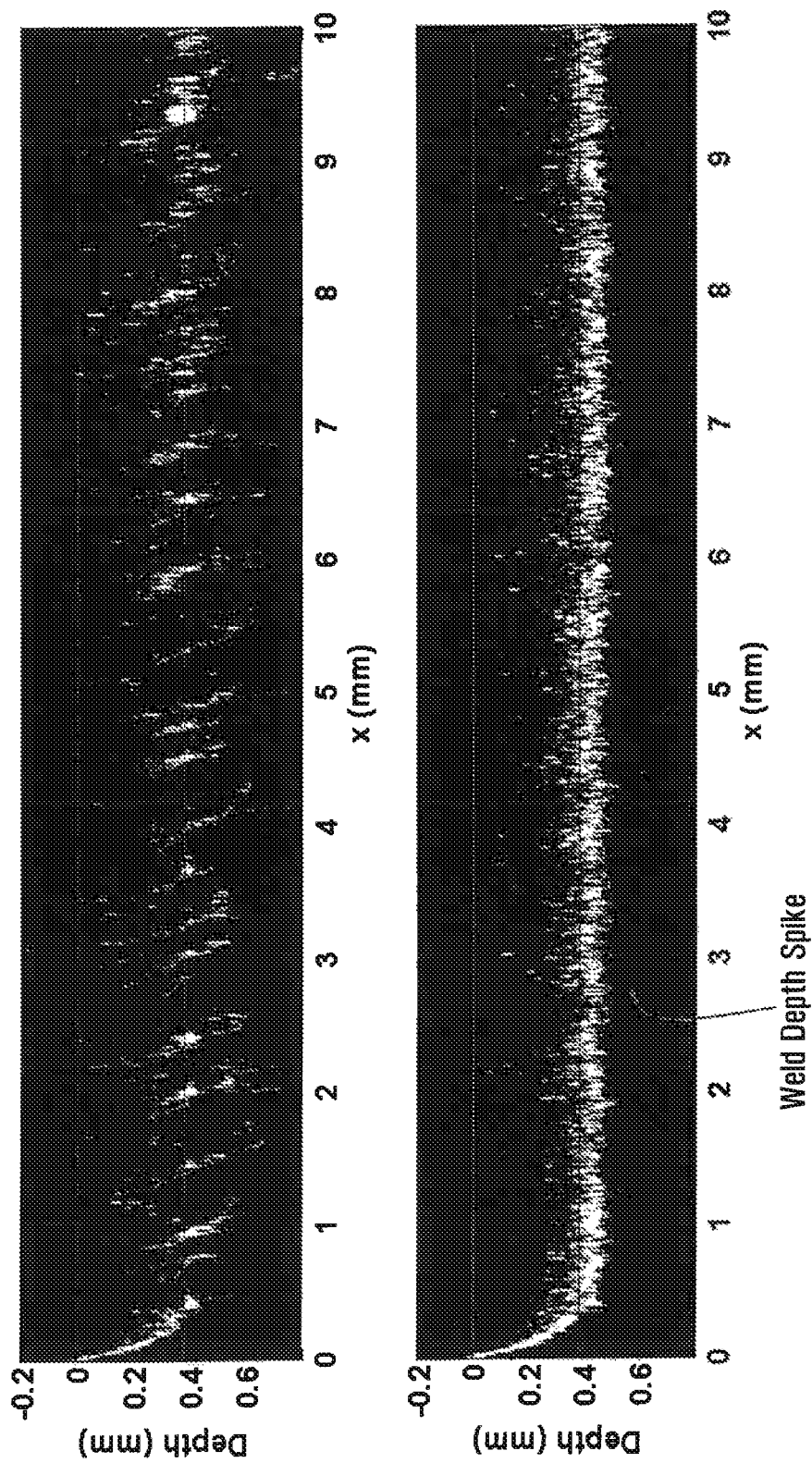
FIG. 10 shows two images of lap welding with digitally tracked keyhole floors, further showing examples of keyhole instability.

Referring now to FIG. 10, in the top view, a coherent image of a lap welding process involving galvanized steel and a 0.015 inch thick stainless steel shim is shown. The material is fed at 60 mm/s and imaged at 230 kHz. The image processor is configured to track the bottom of the keyhole and has overlaid a lighter area to enhance the contrast of the image for easier viewing and interpretation of welding depth. The tracking algorithm locked on to signals 10 standard deviations above the noise floor and used a transverse correlation length of 0.05 mm. Horizontal lines are overlaid showing the thickness of the top sheet. This same underlying tracking information can also be used for numerical interpretation of the keyhole depth and instability. Severe spiking and instability are clearly shown by the large depth swings (amplitudes>0.6 mm are evident over time scales of 5-10 ms and lengths of ~5 mm). This would likely be a defective weld.

In the bottom view, substantially less instability in a similar continuous wave (CW) laser weld is evident. However, there are a few "spikes" visible at 1 mm and just before 2, 3, 4.5, and 8.5 mm. It is more likely that this weld is a good weld than in the top view.

Use of Coherent Imaging in Conjunction with a Mechanically Actuated Lens to Keep the Focus of the Processing Beam a Selected Distance from the Material Surface In some embodiments, one or more of the coherent imaging systems or methods described herein is used in conjunction with a mechanically actuated objective lens to keep the focus of the processing beam a certain distance from the material surface. This approach may be particularly useful in laser cutting embodiments as opposed to welding embodiments. In one example, the focus of the processing beam is mechanically actuated over distances between 0 and 5000 mm along the axis of the beam. This capability is demonstrated without coherent imaging in products such as the Laser Mechanisms FiberCut RA™ (Laser Mechanisms, Inc., Michigan, USA). This may be desirable to correct for non-ideal material geometry (thickness, distortion, etc.) and/or non-ideal motion of the beam delivery system (e.g., a robot that is unable to smoothly move over a plate of metal). If a coherent imaging system were to be added to such a scheme, it could be used instead of, or in addition to, a capacitive height sensor. In this case, the distance of actuation is likely to roughly correspond to a change in the working path length between the coherent imaging system and the material. It may therefore be desirable to change the reference path length of the coherent imaging system in a way that is correlated with the actuation of the processing beam's focus, in order to reduce the relative path length between the sample and reference arms. In most coherent imaging systems, this serves the function of keeping the material surface visible inside of the field of view.

One example of how to produce this correlated reference path length actuation is to digitally synchronize a reference mirror actuator (which may be located some distance away from the beam delivery system itself) to the processing beam focus actuator. An example actuator for the reference arm is an Aerotech PRO115™ linear translation stage (Aerotech, Inc., Pittsburgh, USA). Less expensive and mechanically precise linear actuators may also be used. If the reference path attached to the actuator has multiple passes (i.e., the unidirectional beam path crosses the expanse that is modified by the actuator), then the actuator may be programmed to move a corresponding fraction of the distance moved by the processing beam focal adjuster.

Another example of how to produce the correlated reference path actuation is to use a surface attached to the processing beam focal actuator itself as the reference surface. In this example, some component of the reference path exists inside the beam delivery system and is reflected by a retroreflector or a mirror that is mounted on the processing beam focal actuator. In this way, as the focal position is changed by the actuator, the reference path length is automatically compensated. It may be desirable to mount a lens above the reference surface in the beam delivery head that converges the beam on said reference surface in order to make the coherent imaging signal less sensitive to mechanical imperfections in the focal actuator. The configuration described in this example also provides the benefit of being used as an autofocus system. The focal actuator is programmed via the image processor and feedback controller to keep the material surface at user-defined distance from the zero-delay point in the coherent imaging system.

In order to reduce dispersion mismatch between the reference and sample paths, it is desirable to use approximately equal amounts of each optical material in both paths (this includes air/vacuum). It may be challenging and/or impractical to produce a sufficiently long air path for the reference entirely within the beam delivery system. It may also be very problematic if the process lens, i.e., lens A in FIG. 6 or lens 109 in FIG. 7, was exchanged for one with a different focal length. Therefore, in the example mentioned above, the air component of the reference arm is broken into two sections. The second section is the one that reflects off the processing beam focal actuator as described above. The first section of the reference path is produced at another location inside the coherent imaging system by coupling out of the optical fiber and into the air and then back into fiber before transmitting the reference light to the second section in the beam delivery system. This first part of the path can be adjusted to configure the amount of reference signal power desired, the dispersion characteristics of the reference path, and provide fine adjustment of the zero-delay point relative to the material and/or the focus of the high power processing beam.

In the case that the coherent imaging system does not share the same focal objective as the processing beam, then the focal position of the coherent imaging system may also be actuated axially to keep the focus of the coherent imaging system near the surface of the material being modified.

Figure 6:
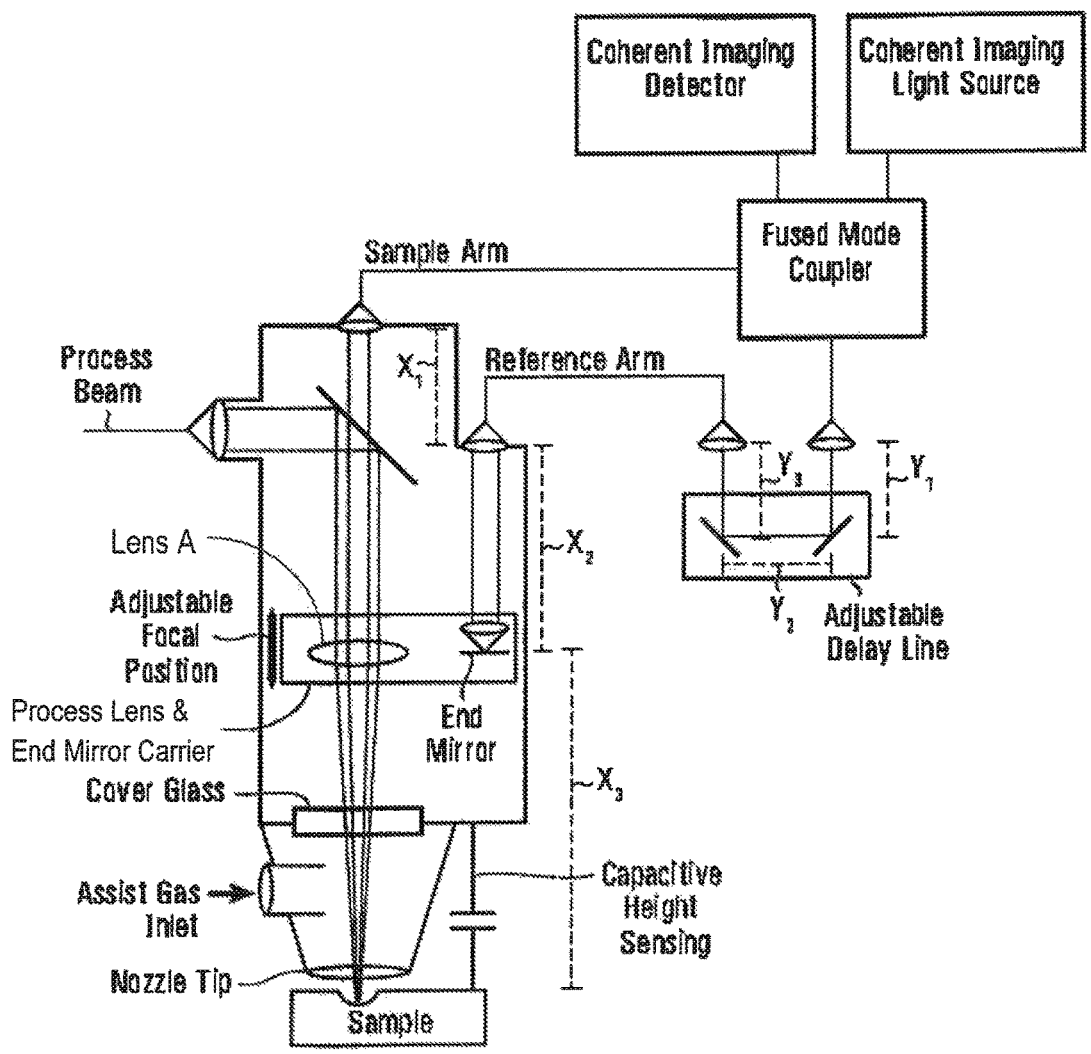
FIG. 6 shows an example of a system with an adjustable delay line in the reference arm.

An example of such a system is depicted in the embodiment of FIG. 6. FIG. 6 shows a reference arm that has an adjustable delay line, and also that has a delay tied to the position of the process lens carrier, an adjustable focal position, and that has capacitive height sensing. More generally, one or more of these features may be implemented. In some embodiments, one or more of these features is implemented in combination with any of the methods/systems described herein.

In FIG. 6:

fiber lengths for sample and reference arms are approximately matched;

not shown is the presence of dispersion compensating media located in the adjustable delay line and/or the nozzle via path x2;

$y1+y2+y3+x2=x1+x2+x3$ (approximately);

as focal position is adjusted dynamically according to the position of the process lens carrier (i.e., location of lens A is shifted vertically), the adjustments are automatically matched by the end mirror located on the same mechanics as lens A;

if the focal length of lens A is changed (e.g., lens A is replaced by a different one), then the lengths of y1, y2, y3 can be changed accordingly, and in some embodiments programmatically;

in some embodiments y1, y2, y3 are adjustable to compensate for changes in gas pressure or other distortions;

distance x2 which forms part of the reference arm tracks movement of the adjustable focal position provided by the process lens and end mirror carrier, and a capacitive height sensing mechanism is provided.

Other Imaging Light Sources

The coherent imaging system may be of the time-domain, spectral domain (i.e., spatially multiplexed spectral measurements) or swept-source (i.e., temporally multiplexed spectral measurements) types. In the first two cases, a superluminescent diode and/or broadband laser (e.g., mode locked Ti:Sapphire, mode locked fiber laser) is an example of an acceptable light sources for coherent imaging. A microelectromechanical system tunable vertical cavity surface emitting laser, and a MEMS (micro-electromechanical system)-tunable VCSEL (vertical cavity surface emitting laser) (see for example Benjamin Potsaid, et al. "MEMS tunable VCSEL light source for ultrahigh speed 60 kHz-1 MHz axial scan rate and long range centimeter class OCT imaging", Proc. SPIE 8213, Optical Coherence Tomography and Coherence Domain Optical Methods in Biomedicine XVI, (Feb. 9, 2012); see also Thorlabs MEMS VCSEL Swept Source OCT System, Thorlabs Inc., Newton, USA). Light sources with very long instantaneous coherence lengths allow for longer imaging ranges that may be particularly beneficial for observing and controlling the material modification processes described herein and those described through reference.

Swept-source and time-domain imaging approaches typically do not use detectors that can substantially discriminate between different frequencies of light. This means that they are more vulnerable to being overloaded by the incoherent emissions of the process and/or by the high power modification energy. The addition of blocking filters, either inside the fiber line (e.g., fiber Bragg gratings, etc.) or at the detector, to isolate the imaging light from the unwanted signals may be employed for the material processing applications described herein. Balanced detection is also substantially beneficial for rejecting these unwanted signals.

Other Material Processing Beam Sources

While the majority of the examples presented here concern fiber-delivered lasers operating in the 1000 to 1100 nm wavelength range, this approach is agnostic to the wavelength of the high powered material modification beam. For example, the wavelength of the modification beam may be between 1 nm and 50 um.

Digital Compensation for DC Signal Changes Arising from Reference Path Actuation In some embodiments of the invention, the reference arm mirrors may be moved in order to adjust the optical path length of the reference arm. Due to precision limitations in the motion control and the sensitivity of energy coupling into single-mode optical fiber, the DC intensity of the reference signal may change with the position of the reference arm delay line. In order to reduce the appearance of fixed pattern noise in the image when the DC power level changes, the background subtraction array may be scaled to match the current DC power level. The amount of scaling can be determined a priori/offline by mapping the DC power level for some set of reference arm positions, or in real time by minimizing the DC power signal (after the signal has been converted from an interferogram) through changing the scaling.

Combining the Processing and Imaging Beams after their Respective Focal Objectives In some embodiments, the processing beam and the imaging beam(s) are combined after their respective focal objectives. Such a system has a beam combining device located distally (i.e., towards the sample) after the focusing devices for the processing and imaging beams. The combiner may be used as a cover glass to segregate other optics from the process gas.

In the case of a high power laser processing beam, the combiner may be, for example, a multilayer dielectrically coated optic that transmits the high power processing beam and reflects the imaging beam. Reflecting the high power processing beam and transmitting the imaging beam is also possible.

The combiner may also be used to sample the intensity of the high power processing beam by directing it to an optical power meter subsystem of the beam delivery system.

Independent lenses allow for scanning both the high power processing beam and the imaging beam and maintaining the alignment of the imaging system relative to the process. Otherwise, chromatic aberrations inherent in the focal lenses might cause the imaging and processing beams to walk off of each other, particularly at larger scan angles.

Figure 7:
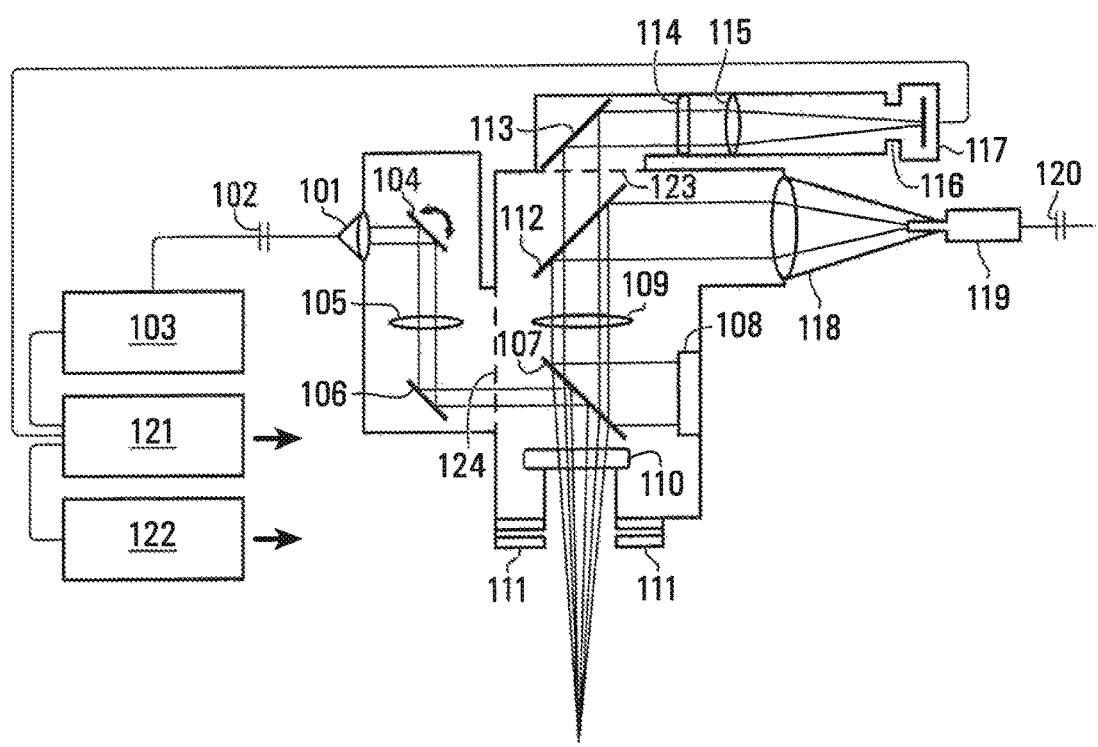
FIG. 7 shows an example of a system with separate objectives for the processing beam and the image beam.

An example of such a system is depicted in FIG. 7. The elements of FIG. 7 include the following:

101. Sample arm collimator for coherent imaging system
102. Fiber delivery of coherent imaging system
103. Coherent imaging unit
121. Feedback controller
122. Process controller
106. Coherent imaging tuning and/or position tuning mirror
104. Galvanometer scanner (1, 2 or 3 axis)
105. Scanning lens for coherent imaging system
107. Combining device for processing and imaging beams
108. Power sensor for processing beam
109. Focusing device for processing beam
110. Cover glass
111. Cross jet/air knife
112. Turning mirror for processing beam
113. Turning mirror for camera port
114. Filter for CCD (charge coupled device) camera
115. CCD camera lens
116. C-mount
117. CCD/CMOS camera
118. High power collimator
119. High power connector
120. High power delivery fiber
123. Camera port
124. Coherent imaging port Not shown is a power control input to the laser, cover gas nozzle, or wire feed/arc tip, any of which may be included in some embodiments.

Mirror 112 in FIG. 7 could optionally be a pair of mirrors and could be motorized to allow for "remote" welding. Element 108 could be a power detector or simply a power absorber. Furthermore, it is noted that either scanning mirror pair, or the adjustable mirror of any of the embodiments described could be replaced with an acousto-optic or electro-optic deflector.

Note that the approach of FIG. 7 has the benefit of not requiring an F-theta lens to be used with the processing beam.

Hybrid Laser Arc Welding

All of the techniques described herein may be applied to observe hybrid laser arc welding or any other material modification process that has a vapor channel/capillary, such as, for example, material liquefaction.

Multiplexing the Reference Arm

In some embodiments of the invention, multiple imaging beams are focused on different areas of the sample. It is not required to have a separate light source and detection scheme for each of these points. Instead, they can be multiplexed onto the same detector (as demonstrated in FIG. 4B). To accomplish this, one may split the sample arm into one or more paths/channels (e.g., by way of an evanescent mode coupler, or multiple internal reflections within an optic) with different optical path lengths. In some cases, the difference in these lengths would be greater than the depth field of view of the coherent imaging system, which may be preferable depending on the application and the number of channels, but not required. The reference arm can be configured to generate one or more reference reflections to correspond to each of these different paths. The actual splitting of the reference arm itself can be accomplished in many ways that would be known to those of ordinary skill in the art (e.g., with semi reflective mirrors, or by splitting the reference into multiple paths each with their own configurable delay), but one must carefully plan the different path lengths to match the expected sample paths during use. Each reference arm path would be configured to add enough additional delay to each channel such that their signals would not overlap. In some embodiments, channels with lower SNRs (e.g., signals from within the keyhole) would be configured to be closer to the zero delay point than those with higher expected SNRs. The result is that each sample image channel would appear at a different location in the processed image and can therefore be simultaneously observed without the need for an entirely separate coherent imaging system.

Another way to effectively multiplex the reference arm is to utilize the secondary coherence subpeaks that are exhibited by some low-coherence light sources (due to residual Fabry-Perot modulation) such as those sold commercially by Superlum (Carrigtwohill, Ireland). These subpeaks create an interference signal typically several millimeters away from the main lobe of the coherence function. This separation can be effectively used as if there was a separate reference surface several millimeters away from the primary one.

In another embodiment of the invention, a birefringent optic (such as a calcite prism) is used to multiplex the imaging beam and spatially separate it onto different parts of the sample. The polarization of the imaging beam into the birefringent optic can then be adjusted to balance the intensity between the two sample paths. Similarly, other birefringent optics can be used in the reference arm to create polarization-specific optical delays for interference comparison and/or to address/access the two polarization channels.

Detection of Surface Composition and/or Quality

Surface composition and/or quality (including, e.g., an indication of oxidation condition, and roughness) is an important factor in the acceptance of a particular material modification process. As the imaging light from a coherent imaging system interacts with the material surface, it can provide a measurement of surface roughness and/or oxidation. This information can be extracted from relative intensity measurements (i.e., comparing signal intensities from different locations and/or different materials) and spectral measurements (i.e. monitoring signal attenuation in a particular region of the imaging spectrum). All of these signals can be processed through the imaging processor and be used to generate various annunciations and process feedback as desired.

Location of Reflecting Interface by Intensity Peak Pixel Identification; Centroid Fitting; Phase and Fringe Evaluation In some embodiments, when processing coherent images, the location of reflecting (and/or scattering) interfaces is determined by locating the depth element with the peak signal intensity (peak pixel identification). In some embodiments, the location of reflecting interfaces is achieved by fitting a quasi-Gaussian curve and extracting its centroid. In some embodiments, the location of reflecting interfaces is achieved by measuring the phase and location of the fringes in the interferogram. In some embodiments, combinations of two or all three of these methods are used to achieve the location of reflecting surfaces. In some embodiments, certain signals are selected and others are disregarded (e.g., in the case of background noise or secondary reflections, to choose a region of interest, or the like).

Interferometry Examples

Interferometry is used throughout the embodiments described herein to generate the measurements discussed. In some embodiments, the interferometer comprises: a combiner; a reference arm, a first component of the imaging light being applied to an input of the reference arm resulting in an output signal of the reference arm, the reference arm having another optical path length; and a sample arm, a second component of the imaging light being applied to the sample arm resulting in an output signal of the sample arm, at least a component of the output signal of the sample arm including reflections of the component of the imaging light from a sample location, the sample arm having at least one optical path length; wherein the combiner combines the output signal of the reference arm and the output signal of the sample arm to produce a combined signal as an interferometry output; the apparatus further comprising a signal detector configured to produce a first interferogram from the interferometry output.

In some embodiments, the apparatus comprises at least one of: multiple sample arms, a respective interferogram being generated for each sample arm, reference arm combination; multiple reference arms, a respective interferogram being generated for each sample arm, reference arm combination; and multiple reference arms and multiple sample arms, a respective interferogram being generated for each sample arm, reference arm combination.

In some embodiments, the interferometer comprises: at least one splitter and/or optical circulator, and at least one sample arm after the splitter and/or optical circulator, the imaging signal being applied to the sample arm resulting in an output signal of the sample arm, at least a component of the output signal of the sample arm including reflections of the component of the imaging signal from at least two locations in the sample arm and/or the material being processed, the sample arm having at least one optical path length and another optical path length; wherein the splitter and/or optical circulator receives the output signal from the sample arm and directs it towards a detector, the apparatus further comprising a signal detector configured to produce an interferogram from the interferometry output.

Figure 8:
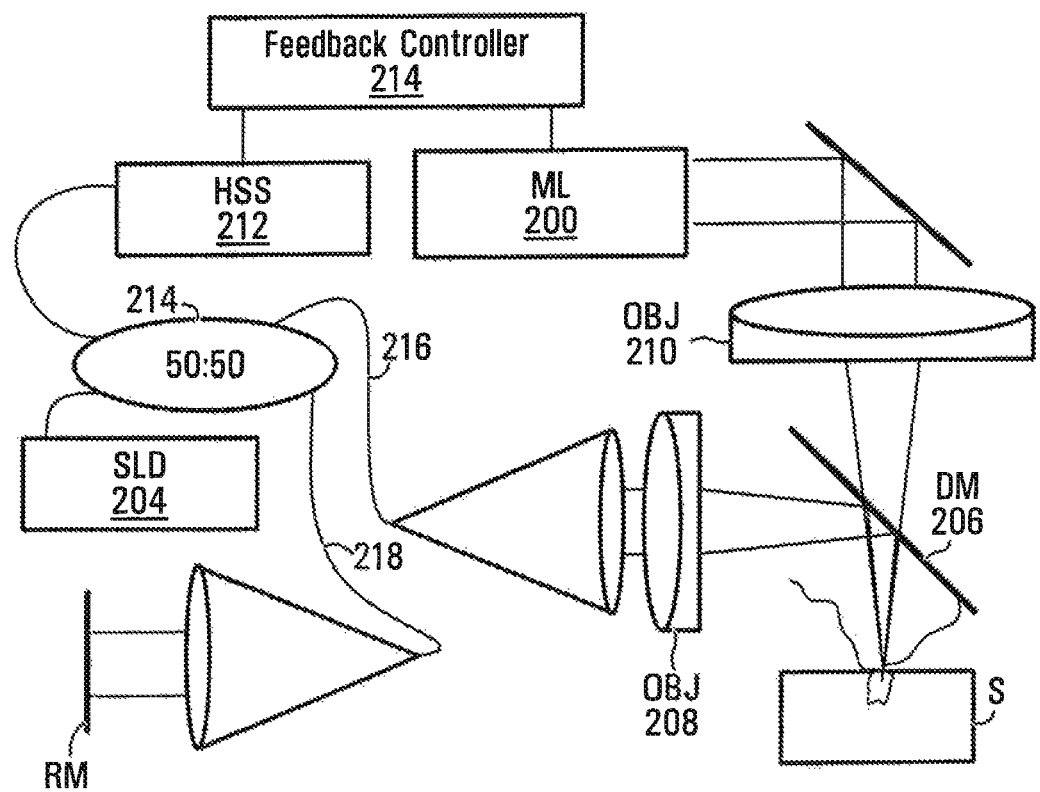
FIGS. 8 and 9 show two example interferometry systems.

FIG. 8 is a block diagram of a first detailed implementation. In this embodiment, modification beam (ML) 200 and imaging beam (SLD) 204 sources are shown. In this embodiment, the two light paths are combined by a dichroic or other combining optic (DM) 206 after independent focal objectives 208, 210. In this embodiment, the interferometer can be built in single or, in other embodiments, in multi-mode optical fibre. Detection is accomplished by means of a high speed spectral detector (HSS) 212. While the embodiment shown uses a 50:50 power splitting ratio 214 between sample arm 216 and reference arm 218, in other embodiments other splitting ratios in the interferometer are possible and may depend on the availability of optical power and/or the need for detection sensitivity. In some embodiments, other interferometer configurations, e.g., Mach-Zehnder, Sagnac, common path, etc. may be used. In this embodiment, DM 206 is shown to reflect the imaging light and transmit the modification light, however, the reverse can alternatively be implemented. In some embodiments, combination of the beams via polarization-sensitive or neutral reflection optics may be implemented. A person of ordinary skill in the art will understand that detection, processing, and feedback electronics are omitted from the embodiment shown in this figure and such processing steps may be performed within the feedback controller. Feedback controller 214 receives the output of the HSS 212 and controls the modification laser 206 and/or one or more other aspects of the material modification process.

Figure 9:
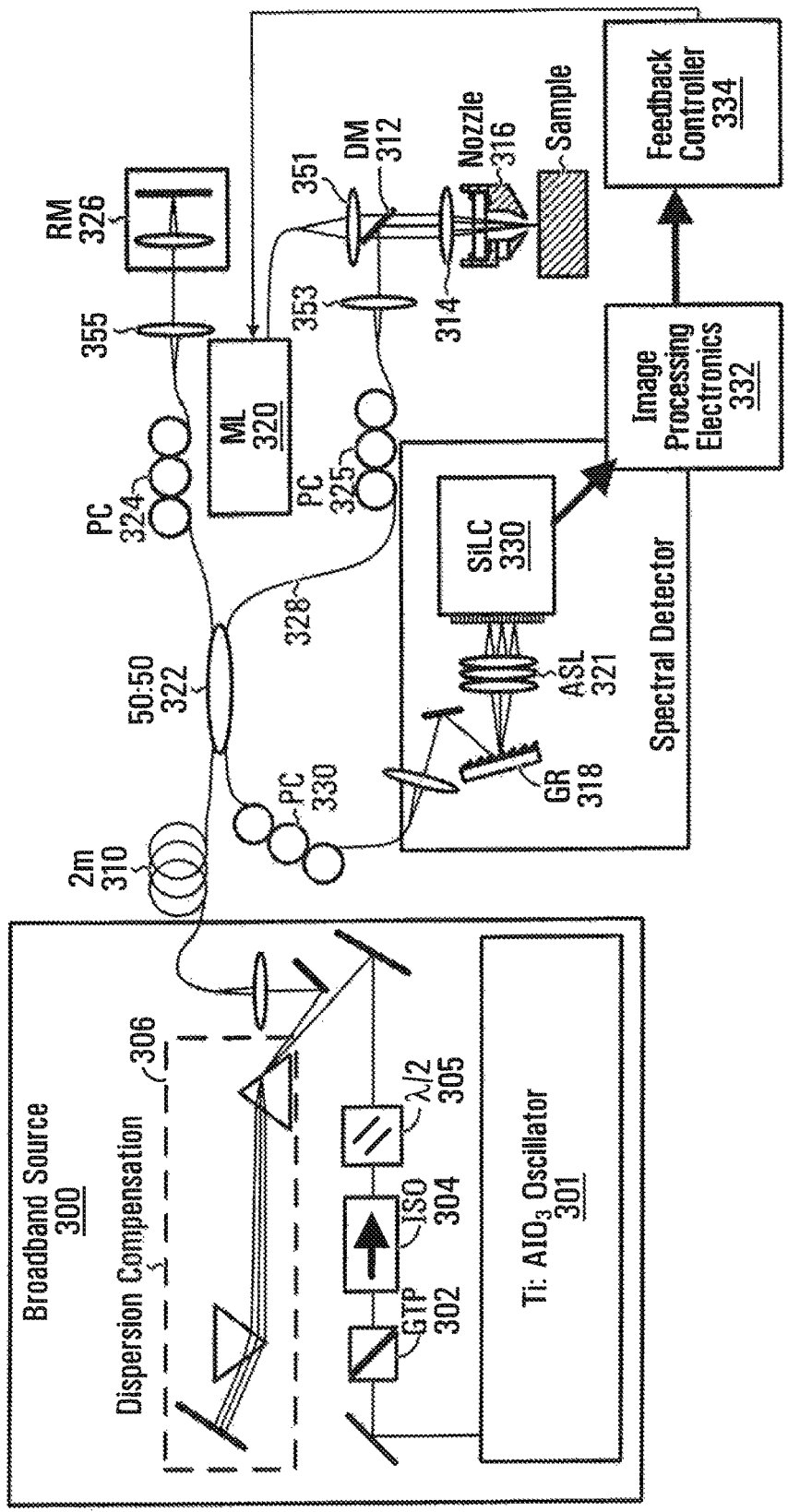

FIG. 9 is a block diagram of a second detailed implementation. In this embodiment, a high power broadband source is created by coupling short, dispersion-optimized pulses output by broadband source 300 into a length of single mode optical fiber 310. This results in an expansion of spectral bandwidth, in some embodiments, on the order of a factor of 6, though in other embodiments, more or less broadening is possible. The embodiment shown features a Ti:AlO3 laser source 301 that operates in the region of 650 to 1100 nm. In other embodiments, spectral ranges from 300 to 15000 nm from other optical imaging sources may be used. In this embodiment, a Glan-Taylor polarizer (GTP) 302, Faraday optical isolator (ISO) 304, half-lambda waveplate polarization control 305, and Fork prism dispersion compensation 306 are shown. In other embodiments, other broadband sources (such as superluminescent diodes, other lasers, and/or other broadening methods) may be substituted for the broadened Ti:AlO3 laser source.

In this embodiment, the modification laser (ML) 320 passes through collimator 351 and the imaging beam passes through sample arm collimator 353 after which the modification laser beam and the imaging beam are combined by an optic component (DM) 312 before they are focused by a common focal objective 314.

In such embodiments, the lens may be achromatic, aspheric, and/or conical (e.g., axicon). This beam combination may be focused through an optional nozzle 316 that can be used to apply assisting fluids (e.g., compressed gas, water spray) to the modification process. The nozzle spray may also be independent from the optical beam; i.e., the two are delivered to the sample from different points. The Michelson interferometer includes a 50:50 splitter 322 (though in other embodiments, other splitting ratios may be used), reference arm collimator 355, and reference mirror 326. Also shown are polarization controllers 324, 325, 330. The spectral detection in this embodiment involves a fiber-coupled reflective grating spectrometer 318. In some embodiments, an additional mirror in front of the lens (ASL) 321 can allow the beam to approach and leave the reflective grating 318 as close to the Littrow configuration as possible, improving diffraction efficiency. In some embodiments, a transmission grating and/or multi-grating, and/or Fabry-Perot spectrometer may be used. A silicon line camera 330 produces an interferogram that is passed to image processing electronics 332, the output of which is passed to feedback controller 334. Feedback controller 334 produces a feedback 336 to control the modification laser 320 or some other aspect of the modification process.

It will be understood that the methods and apparatus described herein may also be used in applications in "remote" welding heads (such as, for example, the Scanlab AG IntelliWELD™ head, Scanlab AG, Germany) where the imaging system is introduced into the camera port of the head. In this case, any splitting or scanning of the imaging beam is still done, but since the processing and imaging beams share the scanning mirrors inside the remote head, the imaging beam is always positioned relative to the processing beam. In other words, the IntelliWELD head's mirrors provide a "common mode" deflection of the imaging and welding beams and an additional scanner/splitter (such as the one depicted in FIG. 3, element 43) produces offsets between the imaging and processing beams for the purposes of imaging various locations in the vicinity of the PCR.

In another embodiment, the remote head utilizes scanning mirrors after the focusing objective (i.e., "post-objective scanning"), thereby minimizing chromatic aberrations and/or chromatic walk-off of the processing and imaging beams that might be present when using an F-theta scan lens.

In some embodiments, an active deflection element (such as the one shown in FIG. 3, element 43) is programmed to deflect the imaging beam by an angle that is related to the current velocity of the processing beam relative to the workpiece. This is because many of the features of interest of the PCR lag behind the processing beam by an amount that is related to the processing velocity. Such dynamic lag control may be particularly acute when the process is changing velocity, magnitude, and/or direction, such as in a curvilinear weld. The amount of lag may be preprogrammed with the process, automatically looked up from a stored table, or dynamically calculated, e.g., from a fitting function that is preprogrammed at the time of manufacturing or adjusted in the field.

In some embodiments, the apparatus may be programmed to automatically search via scanning for a specific PCR feature, and recognize when proper alignment is achieved. For example, proper alignment with the bottom of the vapor channel is achieved when a sufficient/optimal frequency and strength of a reflected signal is detected from a subsurface depth. Through a process of, for example, initial offset estimation, dithering, and successive iterative adjustment, the optimal PCR lag for a linear or curvilinear weld path may be found. Such automatic alignment lends itself to considerable ease of utilizing the embodiments described herein.

Active deflection adjustment and dithering is also useful for maintaining alignment with the PCR if changes to the optics (e.g., arising from vibration, wear, temperature shifts, thermal lensing, or rebuilding of the optics).

Other examples can be found in U.S. patent application Ser. No. 13/245,334, and International Patent Application No. PCT/CA2011/050599, both hereby incorporated by reference in their entirety.

Working Example—First Experiment

A first experiment will be described in the context of the example apparatus of FIG. 3. For the experiment, the laser 17 was a 1070 nm, 1 kW IPG fiber laser, and the laser head 28 was a Laser Mechanisms AccuFiber™ head (Laser Mechanisms, Inc., Michigan, USA). The imaging system 21 was connected to the laser head 28, and produced imaging light having a 840 nm central wavelength (and a bandwidth of approximately 20 nm measured at full-width, half-maximum) which was reflected off a movable mirror 43. A dichroic mirror 45 was used to allow the laser beam and the imaging beam to be directed towards the sample while being closely aligned. A sample of mild steel plate was moved at rates of approximately 20 mm/s in a linear direction 46 while continuous wave keyhole bead on plate welding was performed. Weld depths of approximately 2 mm were achieved. Trials were performed with the imaging beam 20 directed at various positions (e.g., 20a-20e of FIG. 1) relative to the laser beam 16 such that multiple measurements within the keyhole and PCR 30, 32, 34 were obtained.

FIGS. 4A-4E are coherent images of keyhole laser welding. This series of images demonstrates the effect of leading, aligning, or trailing the processing beam with the imaging beam. When the imaging beam leads the processing beam, a poor view of the keyhole depth is achieved in this example, in part because the bottom of the keyhole is poorly illuminated by the imaging beam and in part because much of the imaging light is reflected away and lost by the front wall of the keyhole, never returning to the imaging system. When the imaging beam is aligned with the processing beam, image quality and signal-to-noise ratio (SNR) improves, but there is significant vertical scatter as this location still includes a great deal of the front keyhole wall, which can be quite unstable in the axial direction. Significant improvements to SNR and vertical stability are seen by trailing the processing beam by a fraction of its width. When the processing beam is trailed by an even larger amount, both the top surface and the bottom of the keyhole can be measured. This important capability allows for dynamic determination of the top surface reference points (TSRP) and is useful in cases where there is distortion of the material and/or of the motion system. These images are described in more detail below.

In FIGS. 4A-4E, the x-axis represents time, readings were taken at a rate of 100 kHz (time bins on the x-axis are separated by 10 us), and because the sample was in motion at 60 mm/s, this axis also corresponds to distance along the sample during the weld. The y-axis represents height above the zero delay point of the interferometer. The zero delay point is placed below the surface of the material such that depth is increasing as the signal approaches the zero delay point at the top of the image (labelled 0), i.e., increasing depth is in the upward direction. The black pixels in the image correspond to the depth of the reflection of the imaging beam off the sample surface, darker pixels correspond to a brighter reflection. The black pixels appear to be scattered in part because the keyhole is constantly changing. The diameter of the imaging beam is approximately 70 um and the diameter of the processing beam is approximately 200 um.

Figure 4A:
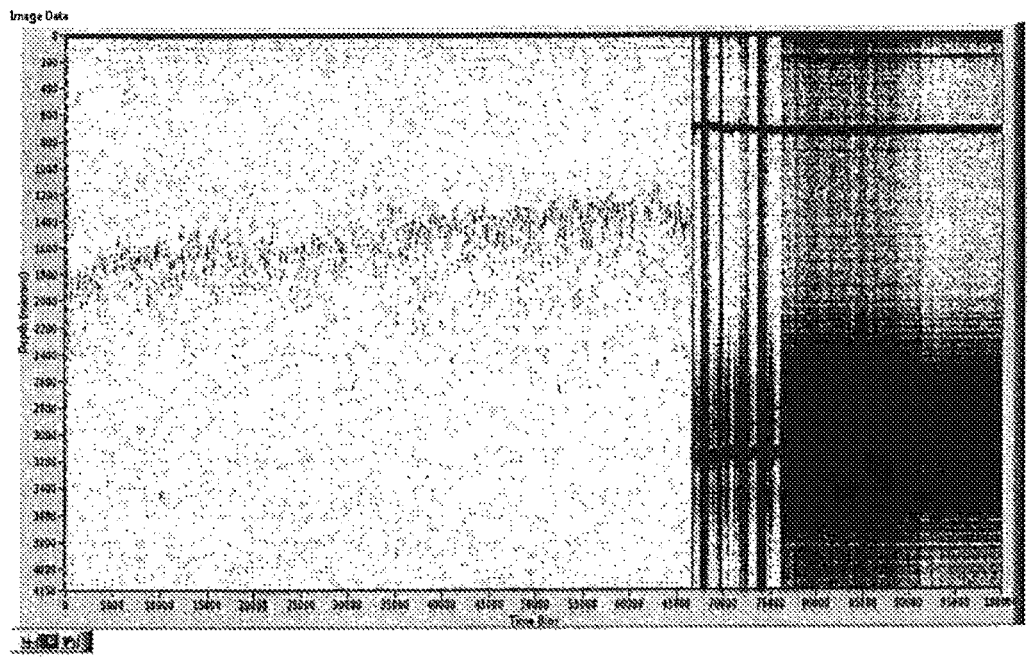
FIGS. 4A-4E depict experimental keyhole imaging image data obtained during welding using a 1.1 kW laser on the sample, a 200 um welding spot, a ~70 um imaging spot, at 20 mm/s, and imaging sample rate of 100 kHz, wherein the imaging beam was leading (FIG. 4A), aligned with (FIG. 4B), or trailing (FIGS. 4C, 4D, 4E) the processing beam.
Figure 4B:
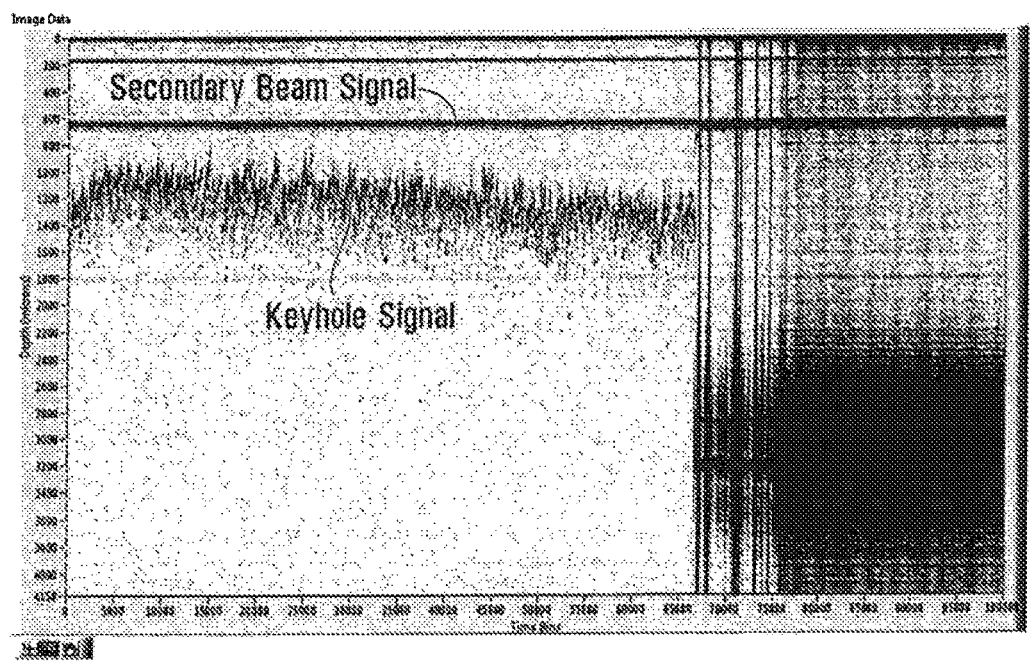

FIG. 4A depicts image data where the imaging beam leads the processing beam by 25 um and roughly corresponds to a position between FIG. 1, 20a and 20c. The sample begins to move and reaches a steady speed before the 0 time mark (left edge of the image). Imaging begins some 100 us before the laser turns on and is used to establish the TSRP of 3624 um. After the laser turns on, a keyhole is rapidly created (in the first 1000 time bins, corresponding to 10 ms) as shown by the black pixels. The keyhole at this position then remains open with measurements of between 1200 urn and 1800 um. This gives a depth reading of approximately 1.8 and 2.4 mm, getting deeper as the weld progresses. The laser turns off at 67500 time bins and the weld terminates and the motion stops after approx. 76000 time bins covering a distance of 45.6 mm. After this time, the imaging system continues to run virgin surface only. In FIG. 4A, the front wall of the keyhole very close to the leading edge is being examined. It can be seen that there is some scatter in the data representing the dynamic variations of the keyhole front wall position and slope.

FIG. 4B depicts image data where the imaging beam aligned with the processing beam and roughly corresponds to position 20b of FIG. 1. This image has a much higher signal to noise ratio (i.e., the signal is brighter), making it easier for a viewer or image processor algorithm to locate the keyhole bottom. As a result, one can more clearly see the initial formation the keyhole as the black pixels move deeper in the first 5000 time bins of the image. The keyhole depth remained fairly constant between 2 and 2.2 mm below the TSRP (located at 2890 um in this image), getting slightly shallower towards the end of the weld. This image also demonstrates a feature of some embodiments of the invention. Here, in addition to the main imaging beam measuring the bottom of the keyhole, a secondary beam path is created by a multiple reflection inside the dichroic (beam combining) mirror. This secondary beam is delayed relative to the first (i.e., appears at a different depth in the image) and impinges on the sample at a separate transverse location substantially outside of the PCR on the virgin metal. This secondary path also creates an interference signal that shows up in the image at the indicated depth 650 µm. Because this transverse location is substantially outside of the PCR, the capability to track the virgin surface simultaneously with imaging the bottom of the keyhole is maintained. This allows for dynamic measurement/calculation of the TSRP and/or height.

Figure 4C:
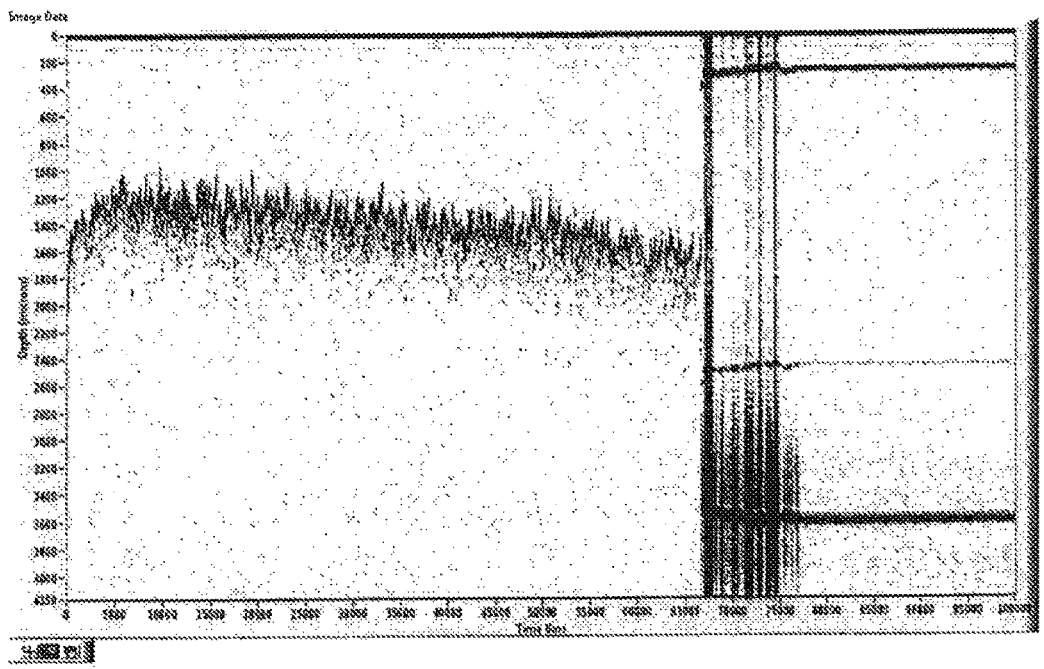

FIG. 4C depicts image data where the imaging beam trails the processing beam by 50 um and roughly corresponds to position 20c of FIG. 1. The TSRP was measured to be at 3120 um in this image. Here the keyhole appears even brighter than in FIG. 4B with a depth of between 2 mm and 2.2 mm. There is less vertical scatter in the image showing that the keyhole has more stability at this 20c location.

Figure 4D:
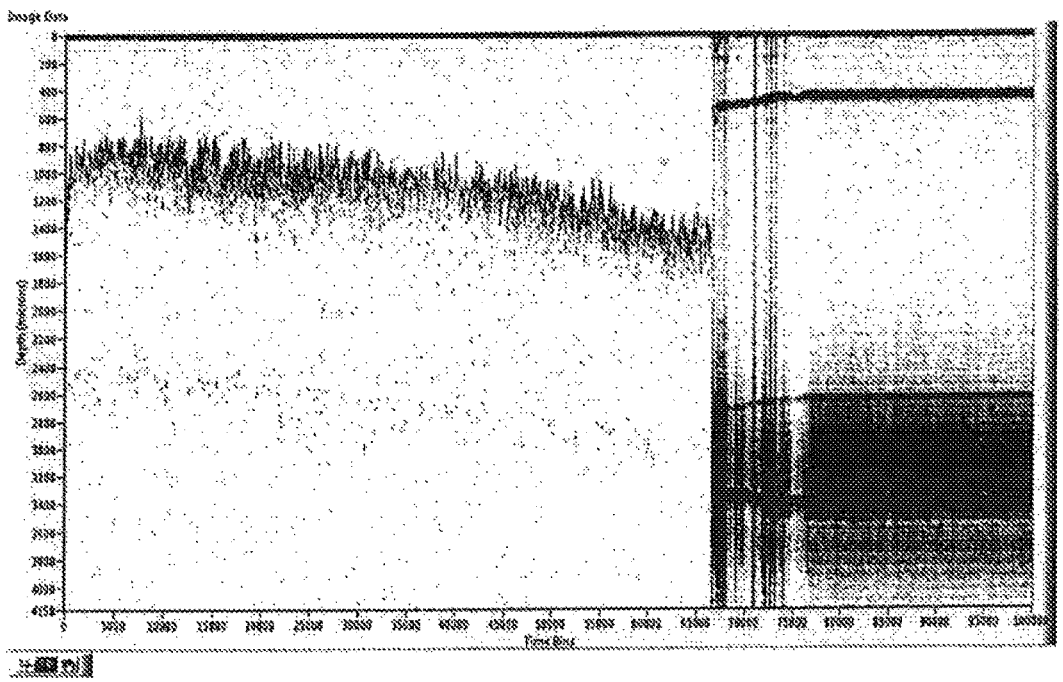

FIG. 4D depicts image data where the imaging beam trails the processing beam by, e.g, 65 um, and roughly corresponds to position 20d of FIG. 1. After initiation the keyhole depth is approximately 2 mm. The TSRP was measured to be at 2700 um at the beginning of the image, and 3400 um at the end of the weld. As a result, the weld depth appears in this image to change by some 700 um across the weld, despite not actually changing. This image illustrates the challenge of applying coherent imaging techniques accurately without a well-defined TSRP. One way of obtaining a TSRP for all points during the image is to assume that the change in TSRP is linear with time and so can be interpolated from the beginning and end TSRPs. In many cases, this is sufficient. Note that this imaging beam is trailing the processing beam sufficiently to illuminate the keyhole bottom and the top surface of the rear of the weld simultaneously. If one draws an imaginary line between time 0, depth 2700 and time 67000 and depth 3400, several (approximately 100) points of enhanced signal can be seen. These are reflections from just behind the keyhole in the region that will form the solidified surface of the weld. Since the top of the weld is at about the same height as the virgin surface of the material, these signals can be used for additional TSRP measurements. This feature of the embodiments is clarified further in the next figure.

Figure 4E:
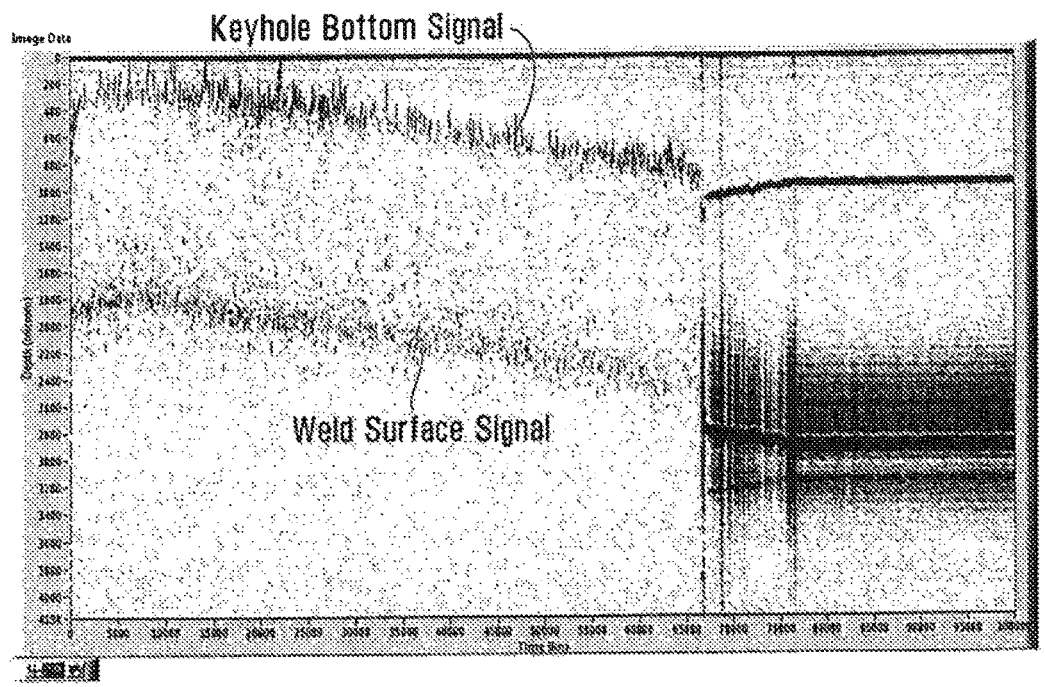

FIG. 4E depicts image data where the imaging beam trails the processing beam by 75 um and roughly corresponds to a position between beams 20d and 20e of FIG. 1, such that both the surface of the weld and the bottom of the keyhole are illuminated at some time. The TSRP was measured to be at 2050 um at the beginning of the image. Here the black pixels are gathered in two bands at different depths. The deeper (closer to 0 in the image) line corresponds to the bottom of the keyhole at the 20c/20d locations. The shallower upper line (in this example the TSRP) corresponds to reflections off the liquid phase of the PCR as would be seen at location 20e. The signal intensity that returns from either region depends on how much of the imaging beam illuminates and reflects from either region. The two bands in the image are the result of the dynamic balance between the signal returning from the two regions. When the keyhole is more narrow, the shallower band of black pixels corresponding to the liquid phase of the PCR at the top of the keyhole is seen more prominently. When the keyhole is wider, more of the bottom is illuminated, enhancing the deeper band black pixels corresponding to the bottom of the keyhole is seen.

From this one can determine that the keyhole front wall is approximately 25 um ahead of the central axis of the processing beam and the back wall varies but is approximately 75 um behind the processing beam, for a total keyhole length of approximately 100 um. One can also calculate the front wall slope by forming an imaginary line between the depth reading in FIGS. 4A and 4B taken at the same (or very nearly the same) instant in time. Other keyhole characteristics can be computed in a similar manner.

Results accuracy can be improved by taking readings at more locations either sequentially through multiple welds with different beam alignments, or dynamically by changing the beam alignment in real time. Other keyhole characteristics can be computed in a similar manner. A leading or trailing imaging spot could also allow measurement of the top surface and bottom surface of the PCR at the same time. Notably, the same approach can be applied to transverse keyhole dynamics just as well as the longitudinal dynamics just discussed.

In some embodiments of the invention, one or more measurement beams will be directed to multiple locations in and near the PCR in rapid succession (perhaps up to 100 kHz or more) by using a movable mirror (depicted as element 43 in FIG. 3) under imaging system control.

In some embodiments, imaging may be done by multiple measurement beams directed at multiple locations simultaneously. In some embodiments, this may be accomplished by multiplexing the imaging beam with a geometric optic such as a multi-faceted mirror and/or a prism.

Working Example—Second Experiment

In another experiment conducted using an apparatus based on FIG. 3, the laser 17 was a 1070 nm, 1 kW IPG fiber laser which was connected to a Laser Mechanisms AccuFiber laser head 28. An imaging light source 21 with a 840 nm wavelength was also connected to the laser head, reflected off a movable mirror 43 and through dichroic mirror 45 used to allow the laser beam and the imaging beam to be directed towards the sample and closely aligned. A sample of mild steel was moved at rates of approximately 1-6 m/min in a linear direction 46 while continuous wave keyhole bead on plate welding was performed. Weld depths of up to 4 mm were achieved. Trials were performed with the imaging beam 20 directed at various positions relative to the laser beam 16 such that measurements within the phase change region (PCR) 30 were obtained.

The results demonstrated that by taking measurements at multiple points within the PCR, information about the maximum weld depth, depth variability, keyhole stability, and weld quality could be obtained. In a specific example, the processing beam incident point is depicted at 41, and this moves with the sample, and the imaging beam is aligned to be incident at a point 42 which trails the processing beam incident point 41 by about 25-75 µm.

This particular approach reduced the vertical scatter of the maximum weld depth measurements substantially when compared to imaging without such an offset. For larger keyholes or those that are deeper with different shapes, the optimum offset will be different and can be determined experimentally. As before, a leading or trailing imaging spot could also allow measurement of the top surface and bottom surface of the PCR at the same time.

In some embodiments, imaging would be done at multiple locations in and near the PCR (depicted in FIG. 1 as imaging beams 20a through 20i) in rapid succession (perhaps up to 100 kHz or more). In some embodiments, this is achieved by using an electronically movable mirror (depicted in FIG. 3 as 43) under imaging system control.

Working Example—Third Experiment

Figure 11:
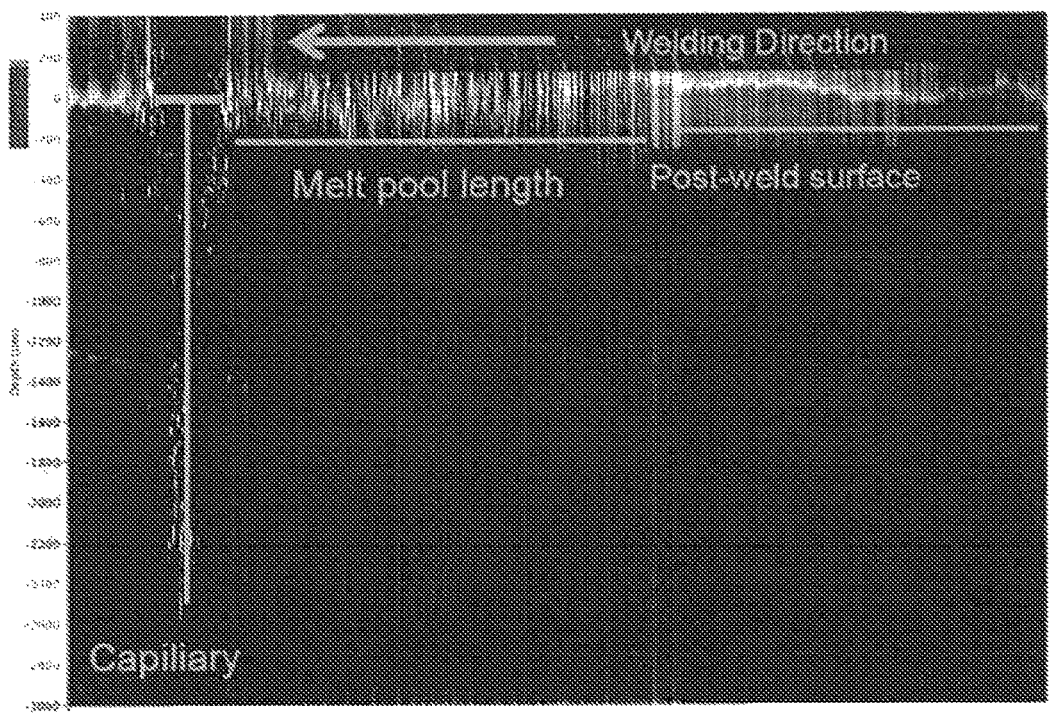
FIG. 11 shows experimental interferometry data from the PCR of a laser weld at a plurality of positions ranging from in front of the processing beam to behind the processing beam.

In a third experiment, an embodiment similar the one shown in FIG. 3 was used to capture an interferometry signal from the PCR of a laser weld at a plurality of positions ranging from in front of the processing beam to behind the processing beam. The result is shown in FIG. 11. Before the processing beam, the information may be used to determine the material position, surface quality, and geometrical compliance of the incoming material. Additionally, scanning using, e.g., FIG. 3, element 43, on another axis may locate a surface feature (e.g., a groove) which can be used to provide seam tracking capabilities before the processing beam.

As the imaging beam is located closer to the processing beam (labelled "capillary" in FIG. 11), it begins to sense the front wall and the bottom of the vapor component (i.e., keyhole) of the PCR. This permits the sensing of many keyhole dynamics such as depth, width, collapse, melt ejection, pore creation, and instability that may be important quality indicators for the process.

As the imaging beam is located behind the processing beam, it begins to sense the melt pool surface. The rapidly changing height of this surface is an indicator of its liquid state since a solid material would not change height so rapidly. Therefore, the length of the surface disruption is indicative of the melt pool length as shown in the figure. The length of this melt pool may be an important indicator of many quality aspects for the process including proper mechanical contact/connection between parts that are to be joined. It may be possible to assume that multiple welds that have the same melt pool length would share similar quality aspects and therefore this information is useful for industrial quality control applications.

As the imaging beam is located further behind the processing beam, the solid surface of the material is sensed. The roughness, height, and depth of this surface may be an important quality indicator. For instance, many surface ripples indicate an unstable weld process that may have created high porosity and therefore compromised hermetic sealing and/or strength.

Furthermore, quantifying the amount of underfill along the surface of the seam is important information for determining the strength of the weld, its resistance to corrosion, and its compatibility with subsequent coating processes such as priming and painting.

As the imaging beam is located even further behind the processing beam, the signal returning from the solid material surface becomes weaker. This is because oxidation of the surface has occurred, making it is less reflective. This information is indicative of cooling rate and shielding gas quality/coverage. Such information may be used, for example, to correct deficiencies in the shielding gas and/or reject parts.

Working Example—Fourth Experiment

Figure 12:
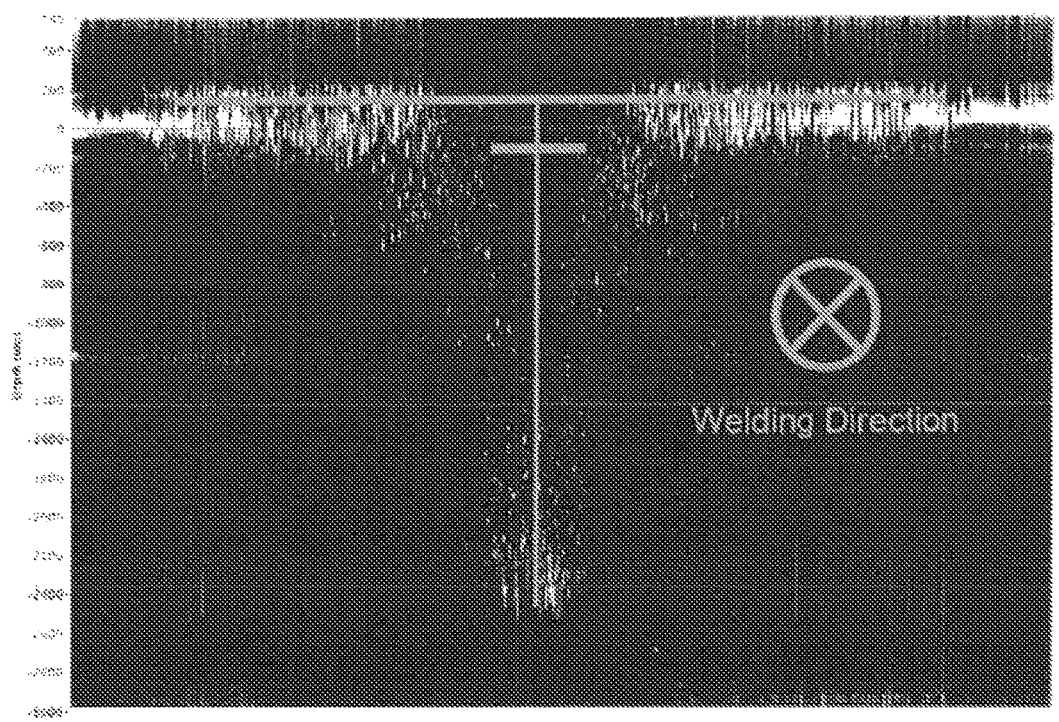
FIG. 12 shows experimental interferometry data from the PCR of a laser weld at a plurality of positions ranging from the left to the right of the processing beam.

In a fourth experiment, an embodiment similar to the one shown in FIG. 3 was used to capture an interferometry signal from the PCR of a laser weld at a plurality of positions ranging from the left to the right of the processing beam. As shown in FIG. 12, the resulting data allows estimation of a number of characteristics of the PCR including the melt pool width, the keyhole width, and keyhole depth.

The width of the melt pool may be an important indicator of many quality aspects for the process, including proper mechanical contact/connection between parts that are to be joined. It may be possible to assume that multiple welds that have the same melt pool length would share similar quality aspects, and therefore this information is useful for industrial quality control applications.

The width of the keyhole and asymmetries thereof may indicate the degree of alignment of the process laser beam with joints of the material being processed (e.g., in a butt or fillet weld) and may therefore be used to guide a seam-tracking process to better process the material.

Working Example—Fifth Experiment

In a fifth experiment, an embodiment similar to the one shown in FIG. 3 was used. For this experiment, the laser 17 was a 1070 nm, 1 kW IPG fibre laser, and the laser head 28 was a Laser Mechanisms AccuFiber™ head. An orthogonal pair of movable mirrors, actuated by galvanometers, was inserted between the collimating lens 22 and the dichroic mirror 43 to enable rapid adjustment of the imaging beam alignment. A sample of stainless steel plate was moved at rates of 5 m/min and 10 m/min while continuous wave keyhole bead on plate welding was performed. Trials were performed with the imaging beam aligned coaxially with the processing beam, as in previous experiments, and with the galvanometer-driven movable mirrors adjusted to place the imaging beam slightly ahead of or behind the processing beam.

FIGS. 13A-13D are coherent images of keyhole laser welding with the imaging beam aligned ahead of or behind the processing beam. Each of these images contains data from two similar welds, performed in opposite directions. These images are oriented with the top surface of the material towards the top of the image, and the zero delay point (at the bottom of the image) deep inside the material. In some cases, the samples have warped with heat; this is visible as a tilt or curvature along the length of each of the two opposite-direction welds in each image.

Figure 13A:
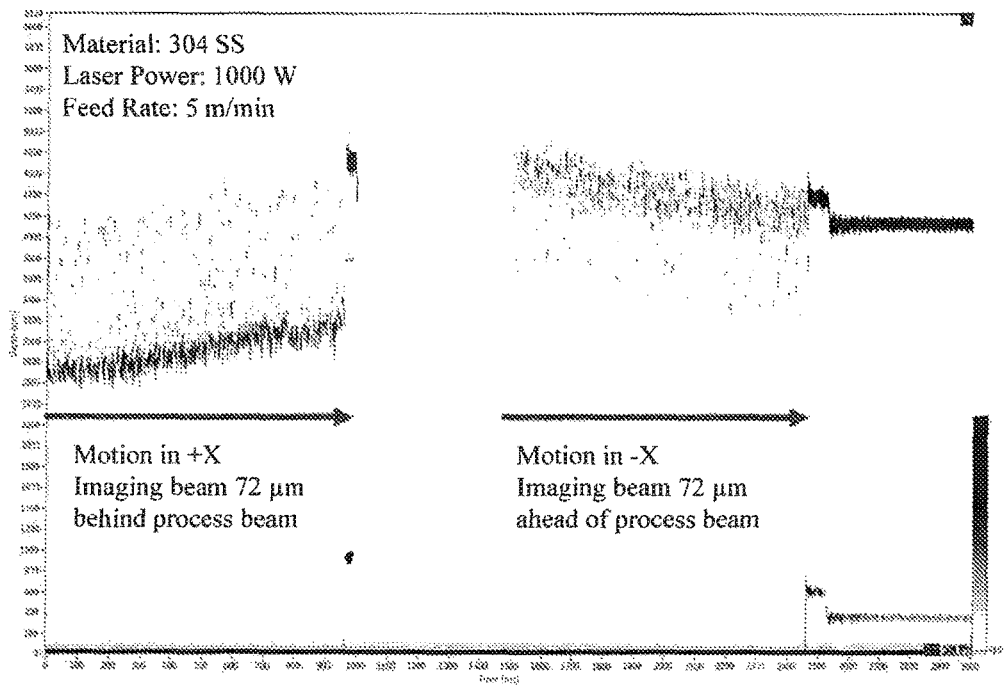
FIGS. 13A-13D are coherent images of keyhole laser welding with the imaging beam aligned ahead of or behind the processing beam.

In FIG. 13A, the welds were performed at 1000 W laser power with a feed rate of 5 m/min. The imaging beam was steered, using the galvanometers, to a focal spot 72 µm behind the processing beam in the first of the two welds. The alignment of the imaging beam was held constant when the direction of travel was reversed for the second weld in this image, so the imaging beam was then 72 µm ahead of the processing beam. At high feed rates, it is expected that the keyhole will lag slightly behind the processing beam. Aligning the imaging beam to a position behind the processing beam led to a stronger signal from the bottom of the keyhole; when the direction was reversed and the imaging beam was ahead of the processing beam, the bottom of the keyhole was not visible and strong signals from near the top of the front wall of the keyhole were obtained.

Figure 13B:
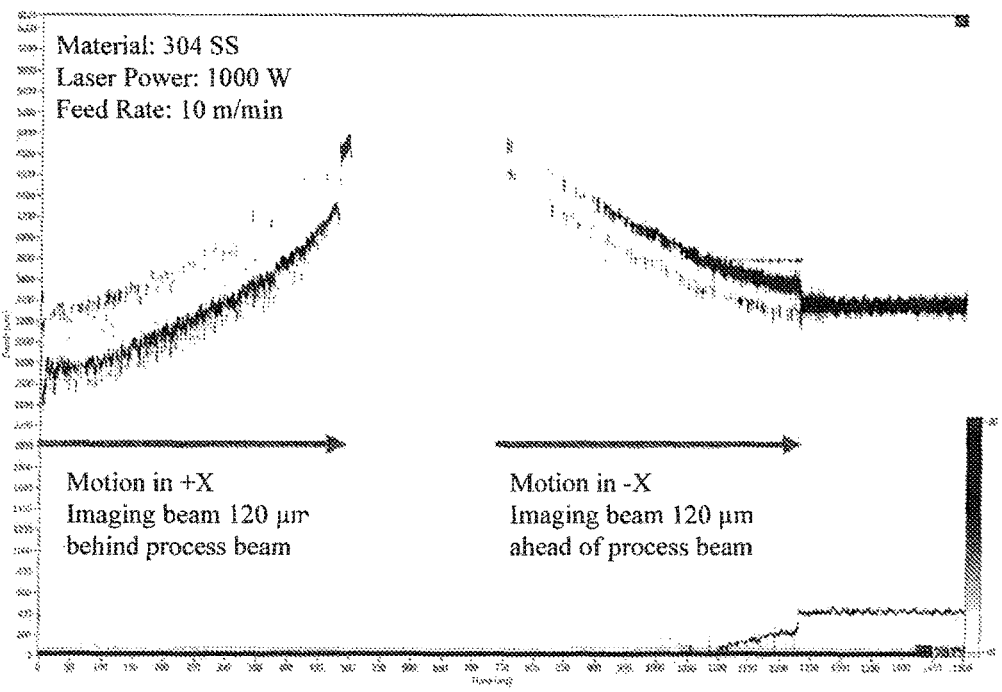

FIG. 13B shows the result of a similar experiment, identical to that of FIG. 13A except for the feed rate (10 m/min instead of 5 m/min) and the imaging beam alignment set by the galvanometers (120 µm behind the processing beam instead of 72 µm). The first of the two welds in this image shows a strong reflection from the bottom of the keyhole, with weaker signals from near the top of the back wall of the keyhole. When the direction was reversed for the second weld, and the imaging beam was leading the processing beam, the signal was dominated by the reflection from the surface of the melt pool ahead of the keyhole, with occasional glimpses of the front wall of the keyhole.

Figure 13C:
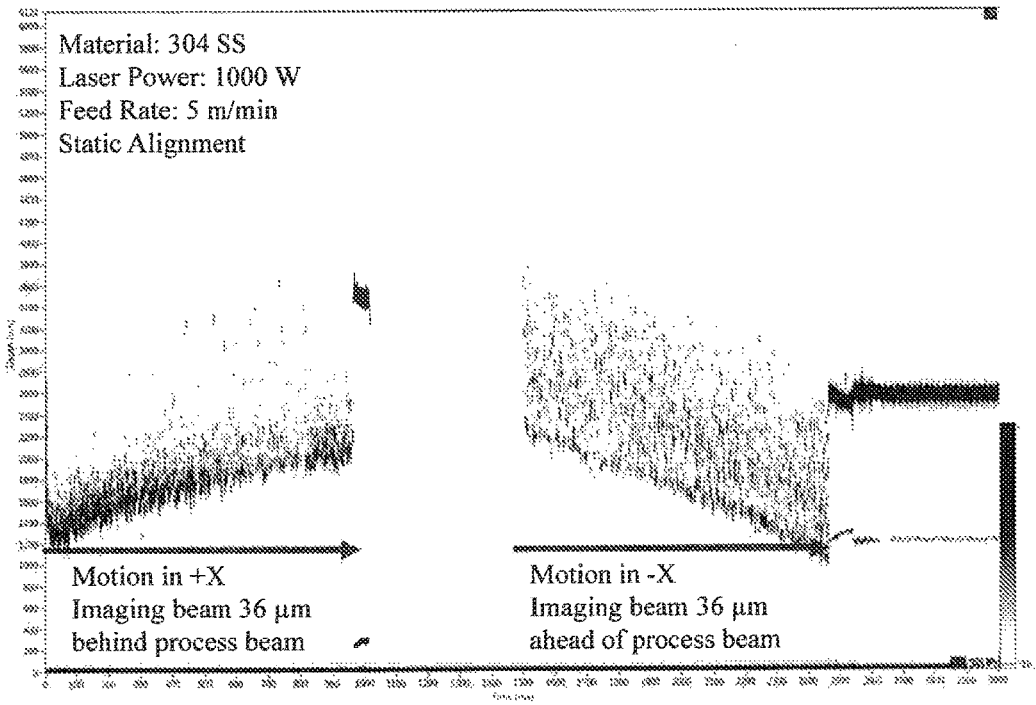
Figure 13D:
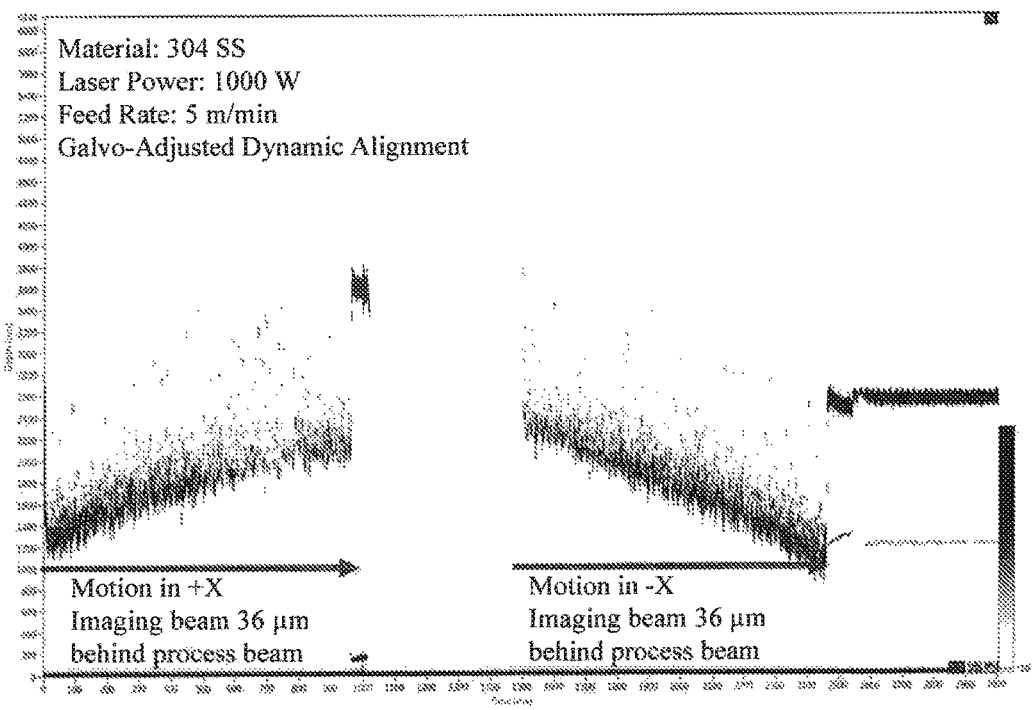

FIGS. 13C and 13D illustrate the difference between fixing the alignment of the imaging beam at a set position relative to the processing beam, and using the galvanometer-actuated mirrors to align the imaging beam at a set distance behind the processing beam given the current direction of travel. The former case (FIG. 13C), the first weld of the pair, performed with the imaging beam slightly lagging the processing beam, yielded a good view of the bottom of the keyhole, but the second weld—performed in the opposite direction—yielded a poor image. In FIG. 13D, the alignment was adapted according to the direction of travel, and welds in both directions yielded images of similar high quality.

Figure 14A:
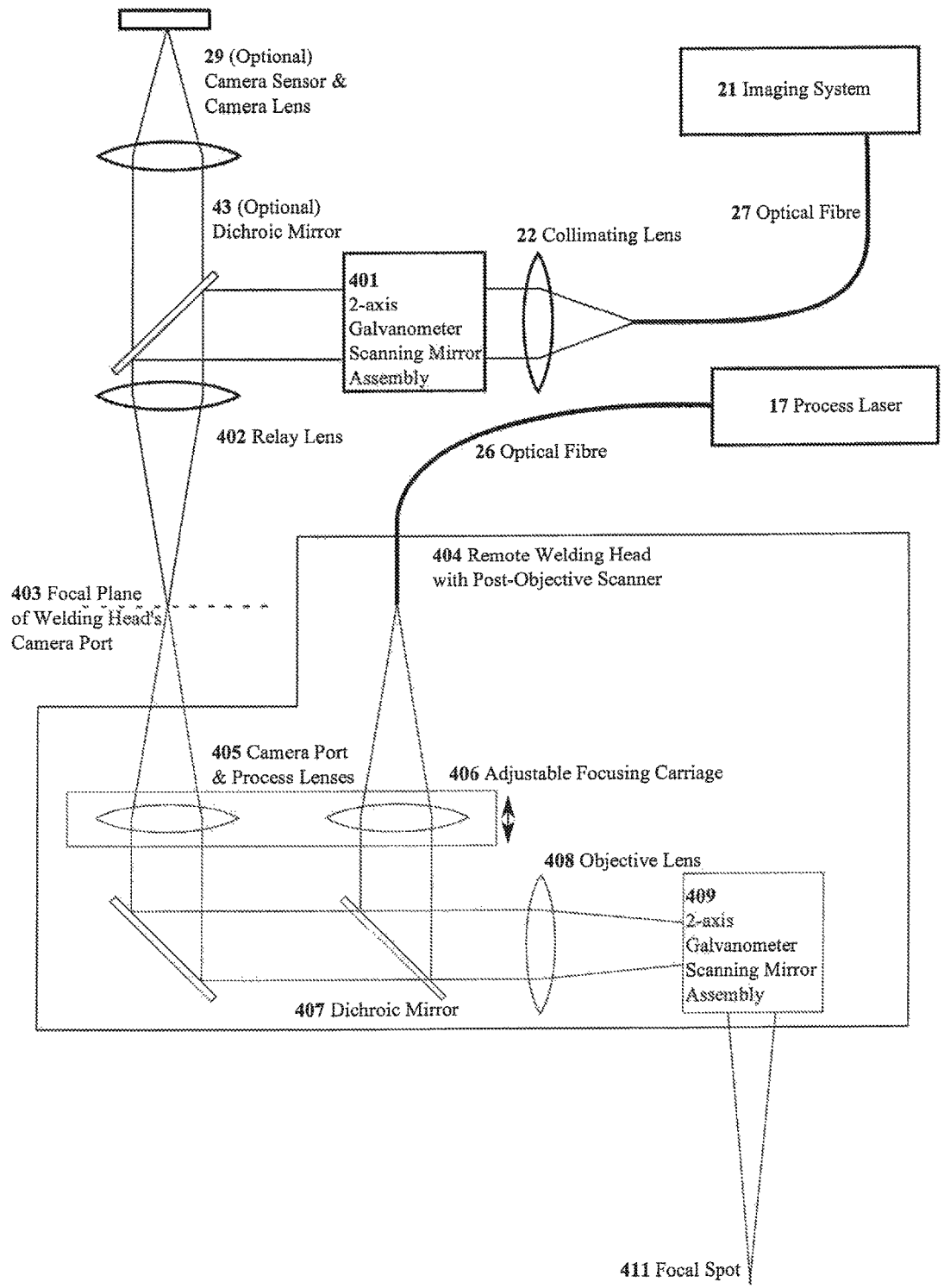
FIGS. 14A and 14B are schematic diagrams of further embodiments of an apparatus that implements keyhole imaging in a material welding process, using a pre-objective scanner (FIG. 14A) or a post-objective scanner (FIG. 14B).
Figure 14B:
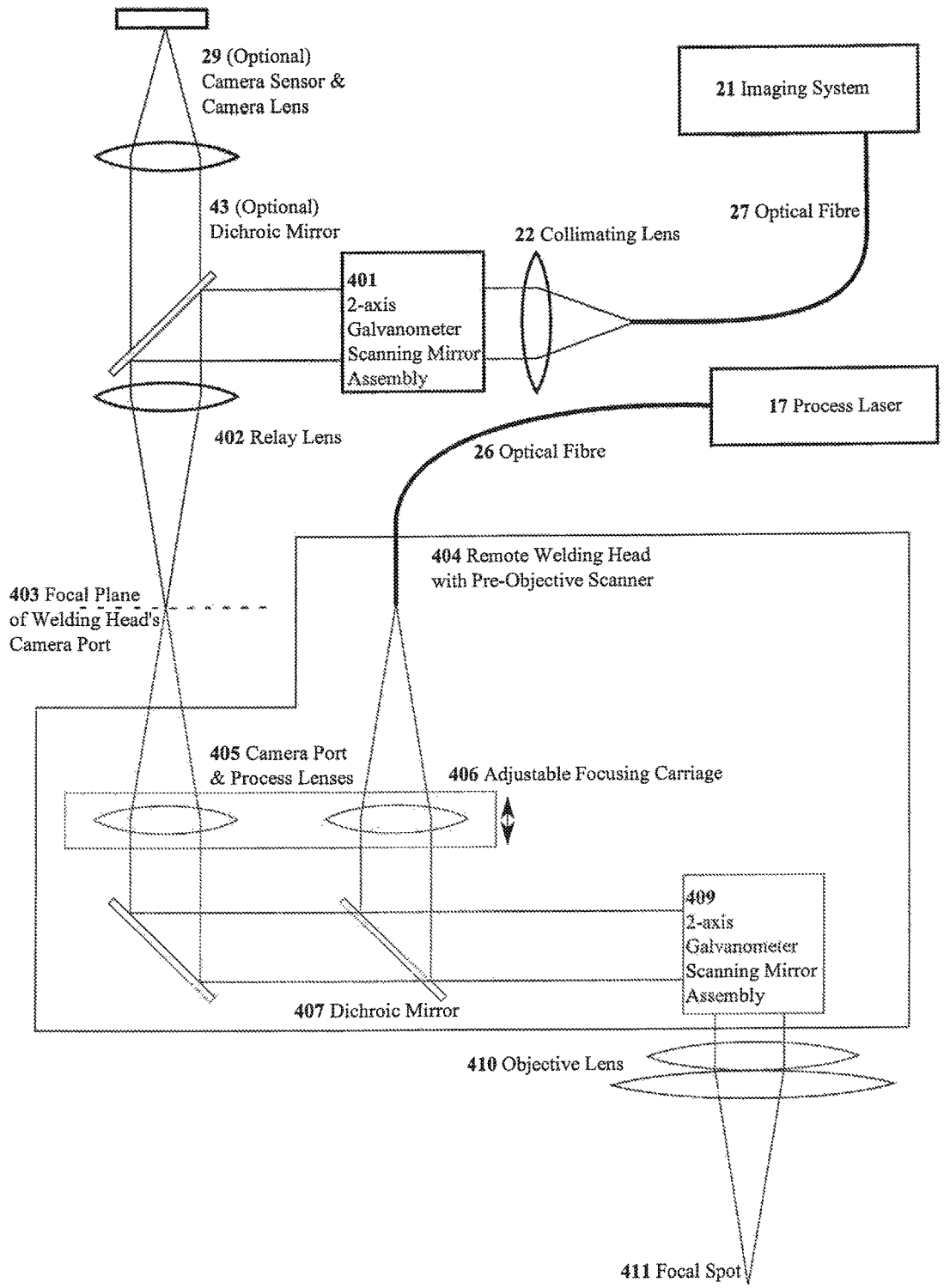

While the effect of lagging/leading with the imaging beam is shown here with linear welds, it is understood that a 2-axis galvanometer mirror system (for example, a Scanlab AG Scancube™ 7 mm) allows this technique to be generalized to 2-D curvilinear welds. It is also understood that this approach may be generalized to "remote" welding heads such as the HighYAG RLSK™ (HIGHYAG Lasertechnologie GmBH, Germany), TRUMPF PFO™ series (TRUMPF Laser-und Systemtechnik GmbH, Germany), and Scanlab AG IntelliWELD™. In one embodiment, illustrated in FIG. 14A for a pre-objective scanner and in FIG. 14B for a post-objective or "F-Theta" scanner, this can be accomplished by using a collimating lens 22, a 2-axis galvanometer scanner 401 and a refocusing lens 402, selected such that the output numerical aperture of this system substantially approximates the supported numerical aperture of the remote head's camera port, to image the fibre core onto the focal plane 403 where a camera sensor would normally be. By synchronizing the motion of this 2-axis galvanometer scanner (and optionally the imaging system's reference arm) with the remote head's motion then the optimal lag between imaging and process beams can be achieved. Programming of this optimal lead/lag can be done manually or automatically through SNR evaluation in iterative and/or dithering processes. Some embodiments of the invention may use a lookup table and/or memory of these optimal lead/lag positions, as functions of the velocity and/or position of the focal spot for various combinations of laser settings, that can be accessed and updated offline or in real time.

EQUIVALENTS

Those of ordinary skill in the art will recognize modifications and variations of the embodiments and examples described herein. It is to be understood that the disclosure may be practiced otherwise than as specifically described herein, within the scope of the appended claims.

The invention claimed is:

1. An apparatus comprising:
a processing beam head configured to be coupled to a process laser that generates a material processing beam for processing a material and creating a phase change region (PCR) in the material, the processing beam head including a primary active deflection device and at least one optical access port;
an imaging optical source optically coupled to the optical access port of the processing beam head, wherein the imaging optical source produces an imaging beam that is directed into the processing beam head via the optical access port and then directed by the processing beam head to at least one imaging beam position in the PCR, wherein the primary active deflection device in the processing beam head deflects the imaging beam together with the processing beam;
a secondary active deflection device optically coupled between the imaging optical source and the optical access port of the processing beam head, wherein the secondary active deflection device only deflects the imaging beam to produce offsets between the imaging beam and the processing beam for imaging various locations in a vicinity of the PCR;
an optical interferometer that produces an interferometry output for each imaging beam position using at least a component of the imaging beam that is directed to the material, wherein the interferometry output is based on at least one optical path length to the material compared to another optical path length; and
an interferometry output processor that processes the interferometry outputs to determine at least one characteristic of the PCR.

2. The apparatus of claim 1 wherein the processing beam head further includes at least one process lens with an adjustable position for adjusting focus of the imaging beam and the processing beam.

3. The apparatus of claim 2 wherein the at least one process lens with adjustable position comprises at least two lenses with adjustable positions for adjusting the focus of the imaging and process beams independently.

4. The apparatus of claim 3 wherein the processing beam head includes an adjustable focusing carriage carrying the two lenses for adjusting the focus of the imaging beam and the processing beam, respectively.

5. The apparatus of claim 1 wherein the secondary active deflection device directs the imaging beam to a selected imaging beam position that is offset relative to the processing beam in the PCR and is selected from at least one previous imaging beam position.

6. The apparatus of claim 1 further comprising a camera coupled to an optical access port of the processing beam head.

7. The apparatus of claim 1 wherein at least one of the active beam deflection devices deflects the imaging beam to a plurality of locations on the material, wherein the interferometry outputs are used to determine material geometry.

8. The apparatus of claim 6 wherein the optical access port is a camera port, and wherein both the camera and the imaging optical source are optically coupled to the processing beam head via the camera port.

9. The apparatus of claim 1 further comprising a collimating lens between the imaging optical source and the secondary active deflection device.

10. The apparatus of claim 9 further comprising at least one lens following the secondary active deflection device, wherein the at least one lens collimates the imaging beam to a beam diameter that is similar to the beam diameter of the processing laser beam.

11. The apparatus of claim 1 wherein the processing beam head includes an objective lens placed such that the primary active beam deflection device is between the objective lens and the material.

12. The apparatus of claim 1 wherein the processing beam head includes an objective lens placed between the primary active beam deflection device and the material.

13. The apparatus of claim 1 wherein the primary and secondary primary active beam deflection devices include 2-axis galvanometer scanning mirror assemblies.

14. The apparatus of claim 1, wherein the at least one characteristic of the PCR comprises at least one of:
keyhole depth; location of maximum keyhole depth; average depth; location; width; length; surface shape; subsurface shape; subsurface keyhole length; subsurface profile; subsurface keyhole width; wall slope; sidewall angle; collapse; instability; dynamics of liquid region of the PCR; location of interface between liquid and solid region; and other physical parameters of the PCR.

15. The apparatus of claim 1, further comprising:
a feedback controller that controls at least one processing parameter of the material modification process based on at least one determined characteristic of the PCR.

16. The apparatus of claim 1, further comprising:
a record generator that records at least one characteristic of the PCR or the material modification process based on the interferometry output.

17. A method comprising:
generating a processing laser beam from a process laser and an imaging beam from a imaging optical source;
coupling the processing laser beam into a processing beam head and coupling the imaging beam into an optical access port of the processing beam head;
deflecting the imaging beam together with the processing laser beam with a primary active deflection device in the processing beam head such that the imaging beam and the processing laser beam are directed to a material, wherein the processing laser beam processes the material and creates a phase change region (PCR) in the material and wherein the imaging beam is reflected from an imaging beam position in the PCR;
deflecting only the imaging beam using a secondary active deflection device before coupling the imaging beam into the optical access port of the processing beam head to produce offsets between the imaging beam and the processing beam for imaging various locations inside of the PCR to measure depth at the various locations inside the PCR;
producing an interferometry output for each imaging beam position using at least a component of the imaging beam that is directed to the material, wherein the interferometry output is based on at least one optical path length to the material compared to another optical path length; and
processing the interferometry outputs to determine at least one characteristic of the PCR.

18. The method of claim 17 further comprising adjusting a focus of the imaging beam and the processing beam in the processing beam head.

19. The method of claim 17 wherein the secondary active deflection device directs the imaging beam to a selected imaging beam position that is offset relative to the processing beam in the PCR and is selected from at least one previous imaging beam position.

20. The method of claim 17 further comprising using the secondary active deflection device to orient the imaging beam to compensate for an offset and/or a lag in one or more characteristics of the PCR relative to the processing beam.

21. The method of claim 17 further comprising determining one or more selected imaging beam positions, based on at least one previous measurement, to be an optimal location to measure the at least one characteristic of the PCR.

22. A method comprising:
generating a processing laser beam from a process laser and an imaging beam from a imaging optical source;
coupling the processing laser beam into a processing beam head and coupling the imaging beam into an optical access port of the processing beam head such that the imaging beam and the processing laser beam are directed to a material, wherein the processing laser beam processes the material and creates a phase change region (PCR) in the material and wherein the imaging beam is reflected from an imaging beam position in the PCR;
deflecting the imaging beam using an active deflection device before coupling the imaging beam into the optical access port of the processing beam head to produce offsets between the imaging beam and the processing beam for imaging various locations inside of the PCR to measure depth at the various locations inside the PCR;
producing an interferometry output for each imaging beam position using at least a component of the imaging beam that is directed to the material, wherein the interferometry output is based on at least one optical path length to the material compared to another optical path length; and
processing the interferometry outputs to determine at least one characteristic of the PCR.

23. An apparatus comprising:
a processing beam head configured to be coupled to a process laser that generates a material processing beam for processing a material and creating a phase change region (PCR) in the material, the processing beam head including at least one optical access port;
an imaging optical source optically coupled to the optical access port of the processing beam head, wherein the imaging optical source produces an imaging beam that is directed into the processing beam head via the optical access port and then directed by the processing beam head to at least one imaging beam position in the PCR;
an active deflection device optically coupled between the imaging optical source and the optical access port of the processing beam head, wherein the active deflection device deflects the imaging beam to produce offsets between the imaging beam and the processing beam for imaging various locations in a vicinity of the PCR;
an optical interferometer that produces an interferometry output for each imaging beam position using at least a component of the imaging beam that is directed to the material, wherein the interferometry output is based on at least one optical path length to the material compared to another optical path length; and
an interferometry output processor that processes the interferometry outputs to determine at least one characteristic of the PCR.

* * * * *